US006303336B1

(12) United States Patent
Spear et al.

(10) Patent No.: US 6,303,336 B1
(45) Date of Patent: Oct. 16, 2001

(54) HERPES VIRUS ENTRY RECEPTOR PROTEIN

(75) Inventors: Patricia G. Spear, Chicago; Rebecca I. Montgomery, Hinsdale, both of IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/333,279

(22) Filed: Jun. 15, 1999

Related U.S. Application Data

(62) Division of application No. 08/509,024, filed on Jul. 28, 1995.

(51) Int. Cl.⁷ .............................. C12P 21/02; C12N 1/21; C12N 5/10

(52) U.S. Cl. ................... 435/69.1; 435/69.7; 435/252.3; 435/325; 435/358; 530/350

(58) Field of Search ................................ 530/350; 514/2; 435/69.1, 69.7, 325, 358, 252.3

(56) References Cited

FOREIGN PATENT DOCUMENTS

WO 96/34095    4/1995   (WO).
WO 98/18824   10/1996   (WO).

OTHER PUBLICATIONS

Stull et al. "Antigene, Ribozyme and Aptamer Nucleic Acid Drugs: Progress and Prospects". Pharmaceutical Research. vol. 12, No. 4:465–481, 1995.*
Gura, Trisha. "Antisense Has Growing Pains". Science. vol. 270:575–577, Oct. 27, 1995.*
Raymond Johnson et al. "Herpes Simplex Virus Glycoprotein D mediates Interference with Herpes Simplex Virus Infection". Journal of Virology. vol. 63, No. 2:819–827, Feb. 1989.*
David C. Johnson et al. "Herpes Simplex Viruses Lacking Glycoprotein D Are Unable To Inhibit Virus Penetration: Quantitative Evidence for Virus–Specific Cell Surface Receptors". Journal of Virology. vol. 62, No. 12: 4605–4612, Dec. 1988.*
Fuller et al. "Anti–glycoprotein D antibodies that permit adsorption but block infection by Herpes simplex virus 1 prevent virion–cell fusion at the cell surface". PNAS. vol. 84:5454–5458, Aug. 1987.*
Kuhn et al. "Identification of Herpes Simplex Virus Type 1 Glycoproteins Interacting with the Cell Surface". Journal of Virology. vol. 64, No. 6:2491–2497, Jun. 1990.*
Shieh et al. "Cell Surface Receptors for Herpes Simplex Virus Are Heparan Sulfate". Journal of Cell Biology. vol. 116:1273–1281, 1992.*
Fields et al. "A novel genetic system to detect protein–protein interactions". Nature. vol. 340:245–246, Jul. 20, 1989.*

Armitage, R.J. (1994). Tumor Necrosis Factor Receptor Superfamily Members And Their Ligands. Current Opin. Immunol. 6, 407–413.
Banfield, B.W., Leduc, Y., Esford, L., Schubert, K., and Tufaro, F. (1995). Sequential Isolation Of Proteoglycan Synthesis Mutants By Using Herpes Simplex Virus As A Selective Agent: Evidence For A Proteoglycan–Independent Virus Entry Pathway. J. Virol. 69, 3290–3298.
Batterson, W. and Roizman, B. (1983). Characterization Of The Herpes Simplex Virion–Associated Factor Responsible For The Induction Of A Genes. J. Virol. 46, 371–377.
Brunetti, C.R., Burke, R.L., Hoflack, B., Ludwig, T., Dingwell, K.S., and Johnson, D.C. (1995). Role Of Mannose–6–Phosphate Receptors In Herpes Simplex Virus Entry Into Cells And Cell–To–Cell Transmission. J. Virol. 69, 3517–3528.
Cai, W., Gu, B., and Person, S. (1988). Role Of Glycoprotein B Of Herpes Simplex Virus Type 1 In Viral Entry And Cell Fusion. J. Virol. 62, 2596–2604.
Campadelli–Fiume, G., Arsenakis, M., Farabegoli, F., and Roizman, B. (1988). Entry Of Herpes Simplex Virus 1 In BJ Cells That Constitutively Express Viral Glycoprotein D Is By Endocytosis And Results In Degradation Of The Virus. J. Virol. 62, 159–167.
Campbell, M.E.M., Palfreyman, J.W., and Preston, C.M. (1984). Identification Of Herpes Simplex Virus DNA Sequences Which Encode A Trans–Acting Polypeptide Responsible For Stimulation Of Immediate Early Transcription. J. Mol. Biol. 180, 1–19.
Corey, L. and Spear, P.G. (1988). Infections With Herpes Simplex Viruses. N. Engl. J. Med. 314, 686–689;–749–757.
Cosman, D. (1994). A Family Of Ligands For The TNF Receptor Superfamily. Stem Cells 12, 440–455.
Dalgliesh, A.G., Beverley, P.C.L., Clapham, P.R., Crawford, D.H., Greaves, M.F., and Weiss, R.A. (1984). The CD4 (T4) Antigen Is An Essential Component Of The Receptor For The AIDS Retrovirus. Nature 312, 763–766.
Dean et al., Single Amino Acid Substitutions in gD of Herpes Simplex Virus 1 Confer Resistance to fD–Mediated Interference and Cause Cell–Type Dependent Alterations in Infectivity. Virology 199, 67–80, 1994.
Ejercito, P.M., Kieff, E., and Roizman, B. (1968). Characterization Of Herpes Simplex Virus Strains Differing in Their Effects On Social Behavior Of Infected Cells. J. Gen. Virol. 2, 357–364.
Feng, Y., Broder, C.C., Kennedy, P.E., and Berger, E.A. (1996). HIV–1 Entry Cofactor. Functional Cdna Cloning Of A Seven–Transmembrane, G Protein–Coupled Receptor. Science 272, 872–877.

(List continued on next page.)

Primary Examiner—Donna C. Wortman
(74) Attorney, Agent, or Firm—Pennie & Edmonds LLP

(57) ABSTRACT

The present invention provides isolated and purified polynucleotides that encode HVEM of mammalian origin, expression vectors containing those polynucleotides, host cells transformed with those expression vectors, a process of making HVEM using those polynucleotides and vectors, and isolated and purified HVEM.

26 Claims, 13 Drawing Sheets

OTHER PUBLICATIONS

Forrester, A., Farrell, H., Wilkinson, G., Kaye, J., Davis–Poynter, N., and Minson, T. (1992). Construction And Properties Of A Mutant Of Herpes Simplex Virus Type 1 With Glycoprotein H Coding Sequences Deleted. J. Virol. 66, 341–348.

Francke, U. and Francke, B. (1981). Requirement Of The Human Chromosome 11 Long Arm For Replication Of Herpes Simplex Virus Type 1 In Nonpermissive Chinese Hamster X Human Diploid Fibroblast Hybrids. Somat. Cell Genet. 7, 171–191.

Fuller, A.O. and Lee, W.–C. (1992). Herpes Simplex Virus Type 1 Entry Through A Cascade Of Virus–Cell Interactions Requires Different Roles Of Gd And Gh In Penetration. J. Virol. 66, 5002–5012.

Gerber, S.I., Belval, B.J., and Herold, B.C. (1995). Differences In The Role Of Glycoprotein C Of HSV–1 And HSV–2 In Viral Binding May Contribute To Serotype Differences in Cell Tropism. Virology 214, 29–39.

Greve, J.M., Davis, G., Meyer, A.M., Forte, C.P., Yost, S.C., Marlor, C.W. Kamarck, M.E., and McClelland, A. (1989). The Major Human Rhinovirus Receptor Is ICAM–1. Cell 56, 839–847.

Heller, R.A. and Kr+nke, M. (1994). Tumor Necrosis Factor Receptor–Mediated Signaling Pathways. J. Cell Biol. 126, 5–9.

Herold, B.C., Gerber, S.I., Belval, B.J., Siston, A.M., and Shulman, N. (1996). Differences In The Susceptibility Of Herpes Simplex Virus Types 1 And 2 To Modified Heparin Compounds Suggest Serotype Differences In Viral Entry. J. Virol. 70, 3461–3469.

Herold, B. C., WuDunn, D., Soltys, N., and Spear, P. G. (1991). Glycoprotein C Of Herpes Simplex Virus Type 1 Plays A Principal Role In The Adsorption Of Virus To Cells And In Infectivity. J. Virol. 65, 1090–1098.

Highlander, S.L., Sutherland, S.L., Gage, P.J., Johnson, D.C., Levine, M., and Glorioso, J.C. (1987). Neutralizing Monoclonal Antibodies Specific For Herpes Simplex Virus Glycoprotein D Inhibit Virus Penetration. J. Virol. 61, 3356–3364.

Ho, D.Y. and Mocarski, E.S. (1988). b–Galactosidase As A Marker In The Peripheral And Neural Tissues Of The Herpes Simplex Virus–Infected Mouse. Virology 167, 279–283.

Johnson, R.M. and Spear, P.G. (1989). Herpes Simplex Virus Glycoprotein D Mediates Interference With Herpes Simplex Virus Infection. J. Virol. 63, 819–827.

Kaner, R.J., Baird, A., Mansukhani, A., Basilico, C., Summers, B.D., Florkiewicz, R.Z., and Hajjar, D.P. (1990). Fibroblast Growth Factor Receptor Is A Portal Of Cellular Entry For Herpes Simplex Virus Type 1. Science 248, 1410–1413.

Karger, A. and Mettenleiter, T.C. (1993). Glycoproteins gIII And gp50 Play Dominant Roles In The Biphasic Attachment Of Pseudorabies Virus. Virology 194, 654–664.

Klatzmann, D., Champagne, E., Chamaret, S., Gruest, J., Guetard, D., Hercend, T., Gluckman, J.–C., and Montagnier, L. (1984). T–lymphocyte T4 Molecule Behaves As The Receptor For Human Retrovirus LAV. Nature 312, 767–768.

Klupp, B.G., Baumeister, J., Karger, A., Visser, N., and Mettenleiter, T.C. (1994). Identification And Characterization Of A Novel Structural Glycoprotein In Pseudorabies Virus, gL. J. Virol. 68, 3868–3878.

Lafferty, W.E., Coombs, R.W., Benedetti, J., Critchlow, C., and Corey, L. (1987). Recurrences After Oral And Genital Herpes Simplex Virus Infection. Influence Of Site Of Infection And Viral Type. N. Engl. J. Med. 316, 1444.

Lee, W.–C. and Fuller, A.O. (1993). Herpes Simplex Virus Type 1 And Pseudorabies Virus Bind To A Common Saturable Receptor On Vero Cells That Is Not Heparan Sulfate. J. Virol. 67, 5088–5097.

Ligas, M.W. and Johnson, D.C. (1988). A Herpes Simplex Virus Mutant In Which Glycoprotein D Sequences Are Replaced By B–Galactosidase Sequences Binds To But Is Unable To Penetrate Into Cells. J. Virol. 62, 1486–1494.

Little, S.P. and Schaffer, P.A. (1981). Expression Of The Syncytial (Syn) Phenotype In HSV–1, Strain KOS: Genetic And Phenotypic Studies Of Mutants In Two Syn Loci. Virology 112, 686–702.

Maddon, P.J., McDougal, J.S., Clapham, P.R., Dalgliesh, A.G., Jamal, S., Weiss, R.A., and Axel, R. (1988). HIV Infection Does Not Rquire Endocytosis Of Its Receptor, CD4. Cell 54, 865–874.

McGeoch, D.J., Dalrymple, M.A., Davison, A.J., Dolan, A., Frame, M.C., McNab, D., Perry, L.J., Scott, J.E., and Taylor, P. (1988). The Complete DNA Sequence Of The Long Unique Region In The Genome Of Herpes Simplex Virus Type 1. J. Gen. Virol. 69, 1531–1574.

Mendelsohn, C.L., Wimmer, E., and Racaniello, V.R. (1989). Cellular Receptor For Poliovirus: Molecular Cloning, Nucleotide Sequence, And Expression Of A New Member Of The Immunoglobulin Superfamily. Cell 56, 855–865.

Mirda, D.P., Navarro, D., Paz, P., Lee, P.L., Pereira, L., and Williams, L.T. (1992). The Fibroblast Growth Factor Receptor Is Not Required For Herpes Simplex Virus Type 1 Infection. J. Virol. 66, 448–457.

Mosialos, G., Birkenbach, M., Yalamanchili, R., VanArsdale, T., Ware, C., and Kieff, E. (1995). The epstein–Barr Virus Transforming Protein LMP1 Engages Signaling Proteins For The Tumor Necrosis Factor Receptor Family. Cell 80, 389–399.

Muggeridge, M.I., Cohen, G.H., and Eisenberg, R.J. (1992). Herpes Simplex Virus Infection Can Occur Without Involvement Of The Fibroblast Growth Factor Receptor. J. Virol. 66, 824–830.

Petrovskis, E.A., Meyer, A.L., and Post, L.E. (1988). Reduced Yield Of Infectious Pseudorabies Virus And Herpes Simplex Virus From Cell Lines Producing Viral Glycoprotein gp50. J. Virol. 62, 2196–2199.

Pogue–Geile, K.L., Lee, G.T.–Y., Shapira, S.K., and Spear, P.G. (1984). Fine Mapping Of Mutations In The Fusion–Inducing MP Strain Of Herpes Simplex Virus Type 1. Virology 136, 100–109.

Pogue–Geile, K.L. and Spear, P.G. (1987). The Single Base Pair Substitution Responsible For The Syn Phenotype Of Herpes Simplex Virus Type 1, Strain MP. Virology 157, 67–74.

Roop, C., Hutchinson, L., and Johnson, D.C. (1993). A Mutant Herpes Simplex Virus Type 1 Unable To Express Glycoprotein L Cannot Enter Cells, And Its Particles Lack Glycoprotein. H. J. Virol. 67, 2285–2297.

Rothe, M., Wong, S.C., Henzel, W.J., and Goeddel, D.V. (1994). A Novel Family Of Putative Signal Transducers Associated With The Cytoplasmic Domain Of The 75 kDa Tumor Necrosis Factor Receptor. Cell 78, 681–692.

Sarmiento, M., Haffey, M.L., and Spear, P.G. (1979). Membrane Proteins Specified By Herpes Simplex Viruses III. Role Of Glycoprotein VP7(B2). J. Virol. 29, 1149–1158.

Shieh, M.-T., WuDunn, D., Montgomery, R.I., Esko, J.D., and Spear, P.G. (1992). Cell Surface Receptors For Herpes Simplex Virus Are Heparan Sulfate Proteoglycans. J. Cell. Biol. 116, 1273–1281.

Shieh, M.-T. and Spear, P.G. (1991). Fibroblast Growth Factor Receptor. Does It Have A Role In The Binding Of Herpes Simplex Virus?. Science 253, 208–210.

Smith, C.A., Farrah, T., and Goodwin, R.G. (1994). The TNF Receptor Superfamily Of Cellular And Viral Proteins: Activation, Costimulation, And Death. Cell 76, 959–962.

Spear, P.G. (1993). Entry Of Alphaherpesviruses Into Cells. Sem. Virol. 4, 167–180.

Staunton, D.E., Merluzzi, V.J., Rothlein, R., Barton, R., Marlin, S.D., and Springer, T.A. (1989). A Cell Adhesion Molecule, ICAM-1, Is The Major Surface Receptor For Rhinoviruses. Cell 56, 849–853.

Subramanian, G., McClain, D.S., Perez, A., and Fuller, A.O. (1994). Swine Testis Cells Contain Functional Heparan Sulfate But Are Defective In Entry Of Herpes Simplex Virus. J. Virol. 68, 5667–5676.

Subramanian, G., LeBlanc, R.A., Wardley, R.C., and Fuller, A.O. (1995). Defective Entry Of Herpes Simplex Virus Types 1 And 2 Into Porcine Cells And Lack Of Infection In Infant Pigs Indicate Species Tropism. J. Gen. Virol. 76, 2375–2379.

Tomassini, J.E., Graham, D., DeWitt, C.M., Lineberger, D.W., Rodkey, J.A., and Colonno, R.J. (1989). cDNA Cloning Reveals That The Major Group Rhinovirus Receptor On Hela Cells Is Intercellular Adhesion Molecule 1. Proc. Natl. Acad. Sci. USA 86, 4907–4911.

Vahlne, A., Svennerholm, B., and Lycke, E. (1979). Evidence For Herpes Simplex Virus Type-Selective Receptors On Cellular Plasma Membranes. J. Gen. Virol. 44, 217–225.

Weiss, R.A. (1993). Cellular receptors and viral glycoproteins involved in retrovirus entry. In The Retroviridae. J.A. Levy, ed. (New York: Plenum Press), pp. 1–72.

Wickham, T.J., Mathias, P., Cheresh, D.A., and Nemerow, G.R. (1993). Integrins Avb3 And Avb5 Promote Adenovirus Internalization But Not Virus Attachment. Cell 73, 309–319.

Wilson, I.A., Niman, H.L., Houghten, R.A., Cherenson, A.R., Connolly, M.L., and Lerner, R.A. (1984). The Structure Of An Antigenic Determinant In A Protein. Cell 37, 767–778.

Wittels, M. and Spear, P.G. (1991). Penetration Of Cells By Herpes Simplex Virus Does Not Require A Low Ph-Dependent Endocytic Pathway. Virus Res. 18, 271–290.

WuDunn, D. and Spear, P.G. (1989). Initial Interaction Of Herpes Simplex Virus With Cells Is Binding To Heparan Sulfate. J. Virol. 63, 52–58.

* cited by examiner

```
  1 CCTTCATACC GGCCCTTCCC CTCGGCTTTG CCTGGACAGC TCCTGCCTCC CGCAGGGCCC
 61 ACCTGTGTCC CCCAGCGCCG CTCCACCCAG CAGGCCTGAG CCCCTCTCTG CTGCCAGACA
121 CCCCCTGCTG CCCACTCTCC TGCTGCTCGG GTTCTGAGGC ACAGCTTGTC ACACCGAGGC
181 GGATTCTCTT TCTCTTTCTC TTCTGGCCCA CAGCCGCAGC AATGGCGCTG AGTTCCTCTG
241 CTGGAGTTCA TCCTGCTAGC TGGGTTCCCG AGCTGCCGGT CTGAGCCTGA GGCATGGAGC
                                                                M E
301 CTCCTGGAGA CTGGGGGCCT CCTCCCTGGA GATCCACCCC AGAACCGAC  GTCTTGAGGC
     P  P  G  D  W  G  P  P  P  W  R  S  T  P  R  T  D  V  L  R
361 TGGTGCTGTA TCTCACCTTC CTGGGAGCCC CCTGCTACGC CCCAGCTCTG CCGTCCTGCA
     L  V  L  Y  L  T  F  L  G  A  P  C  Y  A  P  A  L  P  S  C
421 AGGAGGACGA GTACCCAGTG GGCTCCGAGT GCTGCCCCAA GTGCAGTCCA GGTTATCGTG
     K  E  D  E  Y  P  V  G  S  E  C  C  P  K  C  S  P  G  Y  R
481 TGAAGGAGGC CTGCGGGGAG CTGACGGGCA CAGTGTGTGA ACCCTGCCCT CCAGGCACCT
     V  K  E  A  C  G  E  L  T  G  T  V  C  E  P  C  P  P  G  T
541 ACATTGCCCA CCTCAATGGC CTAAGCAAGT GTCTGCAGTG CCAAATGTGT GACCCAGCCA
     Y  I  A  H  L  N  G  L  S  K  C  L  Q  C  Q  M  C  D  P  A
601 TGGGCCTGCG CGCGAGCCGG AACTGCTCCA GGACAGAGAA CGCCGTGTGT GGCTGCAGCC
     M  G  L  R  A  S  R  N  C  S  R  T  E  N  A  V  C  G  C  S
661 CAGGCCACTT CTGCATCGTC CAGGACGGGG ACCACTGCGC CGCGTGCCGC GCTTACGCCA
     P  G  H  F  C  I  V  Q  D  G  D  H  C  A  A  C  R  A  Y  A
721 CCTCCAGCCC GGGCCAGAGG GTGCAGAAGG GAGGCACCGA GAGTCAGGAC ACCCTGTGTC
     T  S  S  P  G  Q  R  V  Q  K  G  G  T  E  S  Q  D  T  L  C
781 AGAACTGCCC CCCGGGGACC TTCTCTCCCA ATGGGACCCT GGAGGAATGT CAGCACCAGA
     Q  N  C  P  P  G  T  F  S  P  N  G  T  L  E  E  C  Q  H  Q
841 CCAAGTGCAG CTGGCTGGTG ACGAAGGCCG GAGCTGGGAC CAGCAGCTCC CACTGGGTAT
     T  K  C  S  W  L  V  T  K  A  G  A  G  T  S  S  S  H  W  V
901 GGTGGTTTCT CTCAGGGAGC CTCGTCATCG TCATTGTTTG CTCCACAGTT GGCCTAATCA
     W  W  F  L  S  G  S  L  V  I  V  I  V  C  S  T  V  G  L  I
```

FIG.2A

```
961  TATGTGTGAA AAGAAGAAAG CCAAGGGGTG ATGTAGTCAA GGTGATCGTC TCCGTCCAGC
      I  C  V   K  R  R  K   P  R  G   D  V  V   K  V  I   V  S  V  Q

1021 GGAAAAGACA GGAGGCAGAA GGTGAGGCCA CAGTCATTGA GGCCCTGCAG GCCCCTCCGG
      R  K  R   Q  E  A  E   G  E  A   T  V  I   E  A  L  Q   A  P  P

1081 ACGTCACCAC GGTGGCCGTG GAGGAGACAA TACCCTCATT CACGGGGAGG AGCCCAAACC
      D  V  T   T  V  A  V   E  E  T   I  P  S   F  T  G  R   S  P  N

1141 ACTGACCCAC AGACTCTGCA CCCCGACGCC AGAGATACCT GGAGCGACGG CTGCTGAAAG
      H

1201 AGGCTGTCCA CCTGGCGAAA CCACCGGAGC CCGGAGGCTT GGGGGCTCCG CCCTGGGCTG
1261 GCTTCCGTCT CCTCCAGTGG AGGGAGAGGT GGGGCCCCTG CTGGGGTAGA GCTGGGGACG
1321 CCACGTGCCA TTCCCATGGG CCAGTGAGGG CCTGGGGCCT CTGTTCTGCT GTGGCCTGAG
1381 CTCCCCAGAG TCCTGAGGAG GAGCGCCAGT TGCCCCTCGC TCACAGACCA CACACCCAGC
1441 CCTCCTGGGC CAGCCCAGAG GGCCCTTCAG ACCCCAGCTG TCTGCGCGTC TGACTCTTGT
1501 GGCCTCAGCA GGACAGGCCC CGGGCACTGC CTCACAGCCA AGGCTGGACT GGGTTGGCTG
1561 CAGTGTGGTG TTTAGTGGAT ACCACATCGG AAGTGATTTT CTAAATTGGA TTTGAATTCC
1621 GGTCCTGTCT TCTATTTGTC ATGAAACAGT GTATTTGGGG AGATGCTGTG GGAGGATGTA
1681 AATATCTTGT TTCTCCTCAA AAAAAAAAAA AAAAAAAAAA AAAA
```

FIG.2B

```
  1  AAGCTTGCAT GCCTGCAGGT CGACTCTAGC TGGGTTCCCG AGCTGCCGGT CTGAGCCTGA
 61  GGCATGGAGC CTCCTGGAGA CTGGGGGCCT CCTCCCTGGA GATCCACCCC CAGAACCGAC
          M  E   P  P  G   D  W  G  P   P  P  W   R  S  T   P  R  T  D
121  GTCTTGAGGC TGGTGCTGTA TCTCACCTTC CTGGGAGCCC CCTGCTACGC CCCAGCTCTG
      V  L  R   L  V  L   Y  L  T  F   L  G  A   P  C  Y  A   P  A  L
181  CCGTCCTGCA AGGAGGACGA GTACCCAGTG GGCTCCGAGT GCTGCCCCAA GTGCAGTCCA
      P  S  C   K  E  D   E  Y  P  V   G  S  E   C  C  P   K  C  S  P
241  GGTTATCGTG TGAAGGAGGC CTGCGGGGAG CTGACGGGCA CAGTGTGTGA ACCCTGCCCT
      G  Y  R   V  K  E   A  C  G  E   L  T  G   T  V  C   E  P  C  P
301  CCAGGCACCT ACATTGCCCA CCTCAATGGC CTAAGCAAGT GTCTGCAGTG CCAAATGTGT
      P  G  T   Y  I  A   H  L  N  G   L  S  K   C  L  Q   C  Q  M  C
361  GACCCAGCCA TGGGCCTGCG CGCGAGCCGG AACTGCTCCA GGACAGAGAA CGCCGTGTGT
      D  P  A   M  G  L   R  A  S  R   N  C  S   R  T  E  N   A  V  C
421  GGCTGCAGCC CAGGCCACTT CTGCATCGTC CAGGACGGGG ACCACTGCGC CGCGTGCCGC
      G  C  S   P  G  H   F  C  I  V   Q  D  G   D  H  C   A  A  C  R
481  GCTTACGCCA CCTCCAGCCC GGGCCAGAGG GTGCAGAAGG GAGGCACCGA GAGTCAGGAC
      A  Y  A   T  S  S   P  G  Q  R   V  Q  K   G  G  T   E  S  Q  D
541  ACCCTGTGTC AGAACTGCCC CCCGGGGACC TTCTCTCCCA ATGGGACCCT GGAGGAATGT
      T  L  C   Q  N  C   P  P  G  T   F  S  P   N  G  T   L  E  E  C
601  CAGCACCAGA CCAAGTGCAG AATTCACAAG ACCGTTGCAC CCTCGACATG CAGCAAGCCC
      Q  H  Q   T  K  C   R  I  H   K  T  V  A   P  S  T   C  S  K  P
661  ACGTGCCCAC CCCCTGAACT CCTGGGGGGA CCGTCTGTCT TCATCTTCCC CCCAAAACCC
      T  C  P   P  P  E   L  L  G  G   P  S  V   F  I  F   P  P  K  P
721  AAGGACACCC TCATGATCTC ACGCACCCCC GAGGTCACAT GCGTGGTGGT GGACGTGAGC
      K  D  T   L  M  I   S  R  T  P   E  V  T   C  V  V   V  D  V  S
781  CAGGATGACC CCGAGGTGCA GTTCACATGG TACATAAACA ACGAGCAGGT GCGCACCGCC
      Q  D  D   P  E  V   Q  F  T  W   Y  I  N   N  E  Q   V  R  T  A
```

FIG.8A

```
841  CGGCCGCCGC TACGGGAGCA GCAGTTCAAC AGCACGATCC GCGTGGTCAG CACCCTCCCC
      R  P  P    L  R  E    Q  Q  F    N  S  T    I  R  V  V    S  T  L  P

901  ATCACGCACC AGGACTGGCT GAGGGCAAG GAGTTCAAGT GCAAAGTCCA CAACAAGGCA
      I  T  H    Q  D  W    L  R  G  K  E  F  K    C  K  V    H  N  K  A

961  CTCCCGGCCC CCATCGAGAA AACCATCTCC AAAGCCAGAG GGCAGCCCCT GGAGCCGAAG
      L  P  A    P  I  E  K  T  I  S    K  A  R    G  Q  P    L  E  P  K

1021 GTCTACACCA TGGGCCCTCC CCGGGAGGAG CTGAGCAGCA GGTCGGTCAG CCTGACCTGC
      V  Y  T    M  G  P    P  R  E  E    L  S  S    R  S  V    S  L  T  C

1081 ATGATCAACG GCTTCTACCC TTCCGACATC TCGGTGGAGT GGGAGAAGAA CGGGAAGGCA
      M  I  N    G  F  Y  P  S  D  I    S  V  E    W  E  K  N    G  K  A

1141 GAGGACAACT ACAAGACCAC GCCGGCCGTG CTGGACAGCG ACGGCTCCTA CTTCCTCTAC
      E  D  N    Y  K  T    T  P  A  V    L  D  S    D  G  S    Y  F  L  Y

1201 AACAAGCTCT CAGTGCCCAC GAGTGAGTGG CAGCGGGGCG ACGTCTTCAC CTGCTCCGTG
      N  K  L    S  V  P    T  S  E  W    Q  R  G    D  V  F    T  C  S  V

1261 ATGCACGAGG CCTTGCACAA CCACTACACG CAGAAGTCCA TCTCCCGCTC TCCGGGTAAA
      M  H  E    A  L  H    N  H  Y  T    Q  K  S    I  S  R    S  P  G  K

1321 TGAGCGCTGT GCCGGCGAGC TGCCCCTCTC CCTCCCCCCC ACGCCGCAGC TGTGCACCCC
1381 GCACACAAAT AAAGCACCCA GCTCTGCCCT GAACAGCTTC CGGTCTCCCT ATAGTGAGTC
1441 GTATTAATTT CGATAAGCCA GCTGCATTAA TGAATCGGCC AACGCGCGGG GAGAGGCGGT
1501 TTGCGTATTG GGCGCTCTTC CGCTTCCTCG CTCACTGACT CGCTGCGCTC GGTCGTTCGG
1561 CTGCGGCGAG CGGTATCAGC TCACTCAAAG GCGGTAATAC GGTTATCCAC AGAATCAGGG
1621 GATAACGCAG GAAAGAACAT GTGAGCAAAA GGCCAGCAAA AGGCCAGGAA CCGTAAAAAG
1681 GCCGCGTTGC TGGCGTTTTT CCATAGGCTC CGCCCCCCTG ACGAGCATCA CAAAAATCGA
1741 CGCTCAAGTC AGAGGTGGCG AAACCCGACA GGACTATAAA GATACCAGGC GTTTCCCCCT
1801 GGAAGCTCCC TCGTGCGCTC TCCTGTTCCG ACCCTGCCGC TTACCGGATA CCTGTCCGCC
1861 TTTCTCCCTT CGGGAAGCGT GGCGCTTTCT CATAGCTCAC GCTGTAGGTA TCTCAGTTCG
1921 GTGTAGGTCG TTCGCTCCAA GCTGGGCTGT GTGCACGAAC CCCCCGTTCA GCCCGACCGC
1981 TGCGCCTTAT CCGGTAACTA TCGTCTTGAG TCCAACCCGG TAAGACACGA CTTATCGCCA
2041 CTGGCAGCAG CCACTGGTAA CAGGATTAGC AGAGCGAGGT ATGTAGGCGG TGCTACAGAG
2101 TTCTTGAAGT GGTGGCCTAA CTACGGCTAC ACTAGAAGGA CAGTATTTGG TATCTGCGCT
2161 CTGCTGAAGC CAGTTACCTT CGGAAAAAGA GTTGGTAGCT CTTGATCCGG CAAACAAACC
2221 ACCGCTGGTA GCGGTGGTTT TTTTGTTTGC AAGCAGCAGA TTACGCGCAG AAAAAAAGGA
```

FIG.8B

```
2281  TCTCAAGAAG ATCCTTTGAT CTTTTCTACG GGGTCTGACG CTCAGTGGAA CGAAAACTCA
2341  CGTTAAGGGA TTTTGGTCAT GAGATTATCA AAAAGGATCT TCACCTAGAT CCTTTTAAAT
2401  TAAAAATGAA GTTTTAAATC AATCTAAAGT ATATATGAGT AAACTTGGTC TGACAGTTAC
2461  CAATGCTTAA TCAGTGAGGC ACCTATCTCA GCGATCTGTC TATTTCGTTC ATCCATAGTT
2521  GCCTGACTCC CCGTCGTGTA GATAACTACG ATACGGGAGG GCTTACCATC TGGCCCCAGT
2581  GCTGCAATGA TACCGCGAGA CCCACGCTCA CCGGCTCCAG ATTTATCAGC AATAAACCAG
2641  CCAGCCGGAA GGGCCGAGCG CAGAAGTGGT CCTGCAACTT TATCCGCCTC CATCCAGTCT
2701  ATTAATTGTT GCCGGGAAGC TAGAGTAAGT AGTTCGCCAG TTAATAGTTT GCGCAACGTT
2761  GTTGCCATTG CTACAGGCAT CGTGGTGTCA CGCTCGTCGT TTGGTATGGC TTCATTCAGC
2821  TCCGGTTCCC AACGATCAAG GCGAGTTACA TGATCCCCCA TGTTGTGCAA AAAAGCGGTT
2881  AGCTCCTTCG GTCCTCCGAT CGTTGTCAGA AGTAAGTTGG CCGCAGTGTT ATCACTCATG
2941  GTTATGGCAG CACTGCATAA TTCTCTTACT GTCATGCCAT CCGTAAGATG CTTTTCTGTG
3001  ACTGGTGAGT ACTCAACCAA GTCATTCTGA GAATAGTGTA TGCGGCGACC GAGTTGCTCT
3061  TGCCCGGCGT CAATACGGGA TAATACCGCG CCACATAGCA GAACTTTAAA AGTGCTCATC
3121  ATTGGAAAAC GTTCTTCGGG GCGAAAACTC TCAAGGATCT TACCGCTGTT GAGATCCAGT
3181  TCGATGTAAC CCACTCGTGC ACCCAACTGA TCTTCAGCAT CTTTTACTTT CACCAGCGTT
3241  TCTGGGTGAG CAAAAACAGG AAGGCAAAAT GCCGCAAAAA AGGGAATAAG GGCGACACGG
3301  AAATGTTGAA TACTCATACT CTTCCTTTTT CAATATTATT GAAGCATTTA TCAGGGTTAT
3361  TGTCTCATGA GCGGATACAT ATTTGAATGT ATTTAGAAAA ATAAACAAAT AGGGGTTCCG
3421  CGCACATTTC CCCGAAAAGT GCCACCTGAC GTCTAAGAAA CCATTATTAT CATGACATTA
3481  ACCTATAAAA ATAGGCGTAT CACGAGGCCC TTTCGTCTCG CGCGTTTCGG TGATGACGGT
3541  GAAAACCTCT GACACATGCA GCTCCCGGAG ACGGTCACAG CTTGTCTGTA AGCGGATGCC
3601  GGGAGCAGAC AAGCCCGTCA GGGCGCGTCA GCGGGTGTTG GCGGGTGTCG GGGCTGGCTT
3661  AACTATGCGG CATCAGAGCA GATTGTACTG AGAGTGCACC ATATCGACGC TCTCCCTTAT
3721  GCGACTCCTG CATTAGGAAG CAGCCCAGTA GTAGGTTGAG GCCGTTGAGC ACCGCCGCCG
3781  CAAGGAATGG TGCAAGGAGA TGGCGCCCAA CAGTCCCCCG GCCACGGGGC CTGCCACCAT
3841  ACCCACGCCG AAACAAGCGC TCATGAGCCC GAAGTGGCGA GCCCGATCTT CCCCATCGGT
3901  GATGTCGGCG ATATAGGCGC CAGCAACCGC ACCTGTGGCG CCGGTGATGC CGGCCACGAT
3961  GCGTCCGGCG TAGAGGATCT GGCTAGTTAT TAATAGTAAT CAATTACGGG GTCATTAGTT
4021  CATAGCCCAT ATATGGAGTT CCGCGTTACA TAACTTACGG TAAATGGCCC GCCTGGCTGA
4081  CCGCCCAACG ACCCCCGCCC ATTGACGTCA ATAATGACGT ATGTTCCCAT AGTAACGCCA
4141  ATAGGGACTT TCCATTGACG TCAATGGGTG GACTATTTAC GGTAAACTGC CCACTTGGCA
4201  GTACATCAAG TGTATCATAT GCCAAGTACG CCCCCTATTG ACGTCAATGA CGGTAAATGG
4261  CCCGCCTGGC ATTATGCCCA GTACATGACC TTATGGGACT TTCCTACTTG GCAGTACATC
4321  TACGTATTAG TCATCGCTAT TACCATGGTG ATGCGGTTTT GGCAGTACAT CAATGGGCGT
4381  GGATAGCGGT TTGACTCACG GGGATTTCCA AGTCTCCACC CCATTGACGT CAATGGGAGT
4441  TTGTTTTGGC ACCAAAATCA ACGGGACTTT CCAAAATGTC GTAACAACTC CGCCCCATTG
4501  ACGCAAATGG GCGGTAGGCG TGTACGGTGG GAGGTCTATA TAAGCAGAGC TCTCTGGCTA
4561  ACTAGAGAAC CCACTGCTTA ACTGGCTTAT CGAAATTAAT ACGACTCACT ATAGGGAGAC
4621  CC
```

FIG.8C

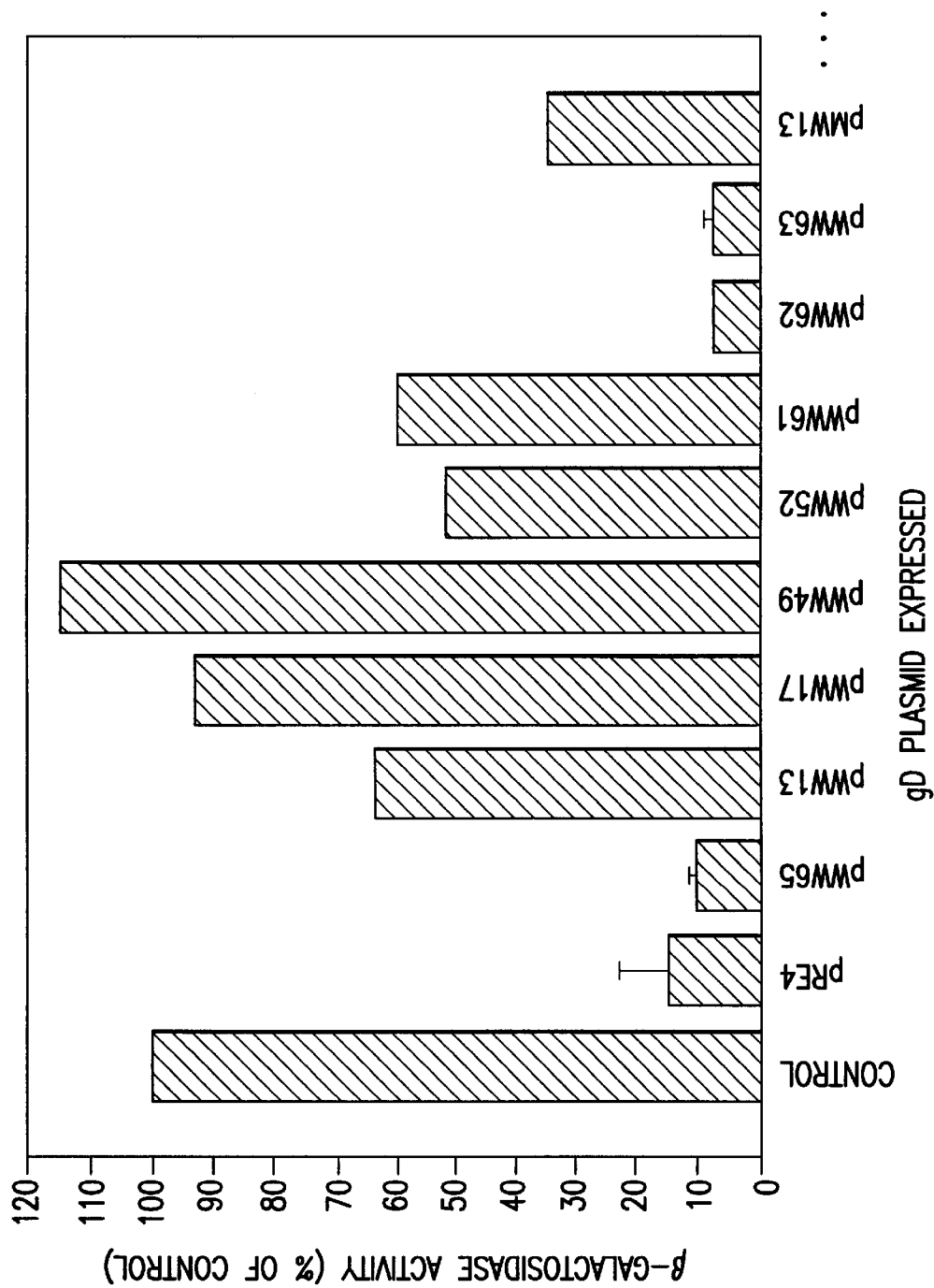

SEQUENCE LISTING

<160> NUMBER OF SEQ ID NOS: 7

<210> SEQ ID NO 1
<211> LENGTH: 1724
<212> TYPE: DNA

-continued

```
<213> ORGANISM: Homo sapiens

<400> SEQUENCE: 1
ccttcatacc ggcccttccc ctcggctttg cctggacagc tcctgcctcc cgcagggccc      60
acctgtgtcc cccagcgccg ctccacccag caggcctgag cccctctctg ctgccagaca     120
cccccctgctg cccactctcc tgctgctcgg gttctgaggc acagcttgtc acaccgaggc    180
ggattctctt tctctttctc ttctggccca cagccgcagc aatggcgctg agttcctctg     240
ctggagttca tcctgctagc tgggttcccg agctgccggt ctgagcctga ggcatggagc     300
ctcctggaga ctgggggcct cctccctgga gatccacccc cagaaccgac gtcttgaggc     360
tggtgctgta tctcaccttc ctgggagccc cctgctacgc cccagctctg ccgtcctgca     420
aggaggacga gtacccagtg ggctccgagt gctgccccaa gtgcagtcca ggttatcgtg     480
tgaaggaggc ctgcggggag ctgacgggca cagtgtgtga ccctgccct ccaggcacct      540
acattgccca cctcaatggc ctaagcaagt gtctgcagtg ccaaatgtgt gacccagcca     600
tgggcctgcg cgcgagccgg aactgctcca ggacagagaa cgccgtgtgt ggctgcagcc     660
caggccactt ctgcatcgtc caggacgggg accactgcgc cgcgtgccgc gcttacgcca     720
cctccagccc gggccagagg gtgcagaagg gaggcaccga gagtcaggac accctgtgtc     780
agaactgccc cccgggggacc ttctctccca atgggaccct ggaggaatgt cagcaccaga    840
ccaagtgcag ctggctggtg acgaaggccg gagctgggac cagcagctcc cactgggtat     900
ggtggtttct ctcaggagc ctcgtcatcg tcattgtttg ctccacagtt ggcctaatca      960
tatgtgtgaa aagaagaaag ccaagggggtg atgtagtcaa ggtgatcgtc tccgtccagc   1020
ggaaaagaca ggaggcagaa ggtgaggcca cagtcattga ggccctgcag gcccctccgg    1080
acgtcaccac ggtggccgtg gaggagacaa tacctcatt cacggggagg agcccaaacc    1140
actgaccac agactctgca ccccgacgcc agagatacct ggagcgacgg ctgctgaaag    1200
aggctgtcca cctggcgaaa ccaccggagc ccggaggctt gggggctccg ccctgggctg    1260
gcttccgtct cctccagtgg agggagaggt ggggccctg ctggggtaga gctggggacg    1320
ccacgtgcca ttcccatggg ccagtgaggg cctgggggcct ctgttctgct gtggcctgag    1380
ctccccagag tcctgaggag gagcgccagt tgccctcgc tcacagacca cacacccagc    1440
cctcctgggc cagcccagag ggcccttcag accccagctg tctgcgcgtc tgactcttgt    1500
ggcctcagca ggacaggccc cggcactgc ctcacagcca aggctggact gggttggctg     1560
cagtgtggtg tttagtggat accacatcgg aagtgatttt ctaaattgga tttgaattcc    1620
ggtcctgtct tctatttgtc atgaaacagt gtatttgggg agatgctgtg ggaggatgta    1680
aatatcttgt ttctcctcaa aaaaaaaaa aaaaaaaaa aaaa                       1724

<210> SEQ ID NO 2
<211> LENGTH: 283
<212> TYPE: PRT
<213> ORGANISM: Homo sapiens

<400> SEQUENCE: 2

Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45
```

```
Val Gly Ser Glu Cys Cys Pro Lys Cys Ser Pro Gly Tyr Arg Val Lys
 50                  55                  60

Glu Ala Cys Gly Glu Leu Thr Gly Thr Val Cys Glu Pro Cys Pro Pro
 65                  70                  75                  80

Gly Thr Tyr Ile Ala His Leu Asn Gly Leu Ser Lys Cys Leu Gln Cys
                 85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280

<210> SEQ ID NO 3
<211> LENGTH: 21
<212> TYPE: DNA
<213> ORGANISM: Homo sapiens

<400> SEQUENCE: 3
aacccggctc gagcggccgc t                                          21

<210> SEQ ID NO 4
<211> LENGTH: 22
<212> TYPE: DNA
<213> ORGANISM: Homo sapiens

<400> SEQUENCE: 4
gaattccacc acacttaagg tg                                         22

<210> SEQ ID NO 5
<211> LENGTH: 19
<212> TYPE: DNA
<213> ORGANISM: Homo sapiens

<400> SEQUENCE: 5
acaagaccgt tgcaccctc                                             19

<210> SEQ ID NO 6
<211> LENGTH: 4622
<212> TYPE: DNA
```

<213> ORGANISM: Homo sapiens

<400> SEQUENCE: 6

| | | | | | |
|---|---|---|---|---|---|
| aagcttgcat | gcctgcaggt | cgactctagc | tgggttcccg | agctgccggt | ctgagcctga | 60 |
| ggcatggagc | ctcctggaga | ctgggggcct | cctccctgga | gatccacccc | cagaaccgac | 120 |
| gtcttgaggc | tggtgctgta | tctcaccttc | ctgggagccc | cctgctacgc | cccagctctg | 180 |
| ccgtcctgca | aggaggacga | gtacccagtg | ggctccgagt | gctgcccaa | gtgcagtcca | 240 |
| ggttatcgtg | tgaaggaggc | ctgcggggag | ctgacgggca | cagtgtgtga | accctgccct | 300 |
| ccaggcacct | acattgccca | cctcaatggc | ctaagcaagt | gtctgcagtg | ccaaatgtgt | 360 |
| gacccagcca | tgggcctgcg | cgcgagccgg | aactgctcca | ggacagagaa | cgccgtgtgt | 420 |
| ggctgcagcc | caggccactt | ctgcatcgtc | caggacgggg | accactgcgc | cgcgtgccgc | 480 |
| gcttacgcca | cctccagccc | gggccagagg | gtgcagaagg | gaggcaccga | gagtcaggac | 540 |
| accctgtgtc | agaactgccc | cccgggggacc | ttctctccca | atgggaccct | ggaggaatgt | 600 |
| cagcaccaga | ccaagtgcag | aattcacaag | accgttgcac | cctcgacatg | cagcaagccc | 660 |
| acgtgcccac | ccctgaact | cctgggggga | ccgtctgtct | tcatcttccc | cccaaaaccc | 720 |
| aaggacaccc | tcatgatctc | acgcaccccc | gaggtcacat | gcgtggtggt | ggacgtgagc | 780 |
| caggatgacc | ccgaggtgca | gttcacatgg | tacataaaca | acgagcaggt | gcgcaccgcc | 840 |
| cggccgccgc | tacgggagca | gcagttcaac | agcacgatcc | gcgtggtcag | cacccctcccc | 900 |
| atcacgcacc | aggactggct | gagggggcaag | gagttcaagt | gcaaagtcca | caacaaggca | 960 |
| ctcccggccc | ccatcgagaa | aaccatctcc | aaagccagag | ggcagcccct | ggagccgaag | 1020 |
| gtctacacca | tgggccctcc | ccgggaggag | ctgagcagca | ggtcggtcag | cctgacctgc | 1080 |
| atgatcaacg | gcttctaccc | ttccgacatc | tcggtggagt | gggagaagaa | cgggaaggca | 1140 |
| gaggacaact | acaagaccac | gccggccgtg | ctggacagca | cggctccta | cttcctctac | 1200 |
| aacaagctct | cagtgcccac | gagtgagtgg | cagcggggcg | acgtcttcac | ctgctccgtg | 1260 |
| atgcacgagg | ccttgcacaa | ccactacacg | cagaagtcca | tctcccgctc | tccgggtaaa | 1320 |
| tgagcgctgt | gccggcgagc | tgcccctctc | cctcccccccc | acgccgcagc | tgtgcacccc | 1380 |
| gcacacaaat | aaagcaccca | gctctgccct | gaacagcttc | cggtctccct | atagtgagtc | 1440 |
| gtattaattt | cgataagcca | gctgcattaa | tgaatcggcc | aacgcgcggg | gagaggcggt | 1500 |
| ttgcgtattg | ggcgctcttc | cgcttcctcg | ctcactgact | cgctgcgctc | ggtcgttcgg | 1560 |
| ctgcggcgag | cggtatcagc | tcactcaaag | gcggtaatac | ggttatccac | agaatcaggg | 1620 |
| gataacgcag | gaaagaacat | gtgagcaaaa | ggccagcaaa | aggccaggaa | ccgtaaaaag | 1680 |
| gccgcgttgc | tggcgttttt | ccataggctc | cgccccctg | acgagcatca | caaaaatcga | 1740 |
| cgctcaagtc | agaggtggcg | aaacccgaca | ggactataaa | gataccaggc | gtttccccct | 1800 |
| ggaagctccc | tcgtgcgctc | tcctgttccg | accctgccgc | ttaccggata | cctgtccgcc | 1860 |
| tttctccctt | cgggaagcgt | ggcgctttct | catagctcac | gctgtaggta | tctcagttcg | 1920 |
| gtgtaggtcg | ttcgctccaa | gctgggctgt | gtgcacgaac | ccccgttca | gcccgaccgc | 1980 |
| tgcgccttat | ccgtaactat | cgtcttgag | tccaacccgg | taagacacga | cttatcgcca | 2040 |
| ctggcagcag | ccactggtaa | caggattagc | agagcgaggt | atgtaggcgg | tgctacagag | 2100 |
| ttcttgaagt | ggtggcctaa | ctacggctac | actagaagga | cagtatttgg | tatctgcgct | 2160 |
| ctgctgaagc | cagttacctt | cggaaaaaga | gttggtagct | cttgatccgg | caaacaaacc | 2220 |
| accgctggta | gcggtggttt | ttttgtttgc | aagcagcaga | ttacgcgcag | aaaaaaagga | 2280 |

```
tctcaagaag atcctttgat cttttctacg gggtctgacg ctcagtggaa cgaaaactca    2340
cgttaaggga ttttggtcat gagattatca aaaaggatct tcacctagat cctttaaat    2400 taaaaatgaa gttttaaatc aatctaaagt atatatgagt aaacttggtc tgacagttac    2460
caatgcttaa tcagtgaggc acctatctca gcgatctgtc tatttcgttc atccatagtt    2520
gcctgactcc ccgtcgtgta gataactacg atacgggagg gcttaccatc tggccccagt    2580
gctgcaatga taccgcgaga cccacgctca ccggctccag atttatcagc aataaaccag    2640
ccagccggaa gggccgagcg cagaagtggt cctgcaactt tatccgcctc catccagtct    2700
attaattgtt gccgggaagc tagagtaagt agttcgccag ttaatagttt gcgcaacgtt    2760
gttgccattg ctacaggcat cgtggtgtca cgctcgtcgt ttggtatggc ttcattcagc    2820
tccggttccc aacgatcaag gcgagttaca tgatccccca tgttgtgcaa aaaagcggtt    2880
agctccttcg gtcctccgat cgttgtcaga agtaagttgg ccgcagtgtt atcactcatg    2940
gttatggcag cactgcataa ttctcttact gtcatgccat ccgtaagatg cttttctgtg    3000
actggtgagt actcaaccaa gtcattctga gaatagtgta tgcggcgacc gagttgctct    3060
tgcccggcgt caatacggga taataccgcg ccacatagca gaactttaaa agtgctcatc    3120
attggaaaac gttcttcggg gcgaaaactc tcaaggatct taccgctgtt gagatccagt    3180
tcgatgtaac ccactcgtgc acccaactga tcttcagcat cttttacttt caccagcgtt    3240
tctgggtgag caaaaacagg aaggcaaaat gccgcaaaaa agggaataag ggcgacacgg    3300
aaatgttgaa tactcatact cttcctttt caatattatt gaagcattta tcagggttat    3360
tgtctcatga gcggatacat atttgaatgt atttagaaaa ataaacaaat aggggttccg    3420
cgcacatttc cccgaaaagt gccacctgac gtctaagaaa ccattattat catgacatta    3480
acctataaaa ataggcgtat cacgaggccc tttcgtctcg cgcgtttcgg tgatgacggt    3540
gaaaacctct gacacatgca gctcccggag acggtcacag cttgtctgta agcggatgcc    3600
gggagcagac aagcccgtca gggcgcgtca gcgggtgttg gcgggtgtcg ggctggctt    3660 aactatgcgg catcagagca gattgtactg agagtgcacc atatcgacgc tctcccttat    3720
gcgactcctg cattaggaag cagcccagta gtaggttgag gccgttgagc accgccgccg    3780
caaggaatgg tgcaaggaga tggcgcccaa cagtccccg gccacggggc ctgccaccat    3840
acccacgccg aaacaagcgc tcatgagccc gaagtggcga gcccgatctt ccccatcggt    3900
gatgtcggcg atataggcgc cagcaaccgc acctgtggcg ccggtgatgc cggccacgat    3960
gcgtccggcg tagaggatct ggctagttat taatagtaat caattacggg gtcattagtt    4020
catagcccat atatggagtt ccgcgttaca taacttacgg taaatggccc gcctggctga    4080
ccgcccaacg accccgccc attgacgtca ataatgacgt atgttcccat agtaacgcca    4140
atagggactt tccattgacg tcaatgggtg gactatttac ggtaaactgc ccacttggca    4200
gtacatcaag tgtatcatat gccaagtacg cccctattg acgtcaatga cggtaaatgg    4260
cccgcctggc attatgccca gtacatgacc ttatgggact ttcctacttg gcagtacatc    4320
tacgtattag tcatcgctat taccatggtg atgcggtttt ggcagtacat caatgggcgt    4380
ggatagcggt ttgactcacg gggatttcca agtctccacc ccattgacgt caatgggagt    4440
ttgttttggc accaaaatca acgggacttt ccaaaatgtc gtaacaactc cgccccattg    4500
acgcaaatgg gcggtaggcg tgtacggtgg gaggtctata taagcagagc tctctggcta    4560
actagagaac ccactgctta actggcttat cgaaattaat acgactcact ataggagac    4620
``` cc                                                                                                    4622

<210> SEQ ID NO 7
<211> LENGTH: 419
<212> TYPE: PRT
<213> ORGANISM: Homo sapiens

<400> SEQUENCE: 7

Met Glu Pro Pro Gly Asp Trp Gly Pro Pro Trp Arg Ser Thr Pro
 1               5                  10                  15

Arg Thr Asp Val Leu Arg Leu Val Leu Tyr Leu Thr Phe Leu Gly Ala
                 20                  25                  30

Pro Cys Tyr Ala Pro Ala Leu Pro Ser Cys Lys Glu Asp Glu Tyr Pro
             35                  40                  45

Val Gly Ser Glu Cys Cys Pro Lys Cys Ser Pro Gly Tyr Arg Val Lys
         50                  55                  60

Glu Ala Cys Gly Glu Leu Thr Gly Thr Val Cys Glu Pro Cys Pro Pro
 65                  70                  75                  80

Gly Thr Tyr Ile Ala His Leu Asn Gly Leu Ser Lys Cys Leu Gln Cys
                 85                  90                  95

Gln Met Cys Asp Pro Ala Met Gly Leu Arg Ala Ser Arg Asn Cys Ser
                100                 105                 110

Arg Thr Glu Asn Ala Val Cys Gly Cys Ser Pro Gly His Phe Cys Ile
            115                 120                 125

Val Gln Asp Gly Asp His Cys Ala Ala Cys Arg Ala Tyr Ala Thr Ser
        130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Arg Ile His Lys Thr Val Ala
                180                 185                 190

Pro Ser Thr Cys Ser Lys Pro Thr Cys Pro Pro Glu Leu Leu Gly
            195                 200                 205

Gly Pro Ser Val Phe Ile Phe Pro Pro Lys Pro Lys Asp Thr Leu Met
    210                 215                 220

Ile Ser Arg Thr Pro Glu Val Thr Cys Val Val Val Asp Val Ser Gln
225                 230                 235                 240

Asp Asp Pro Glu Val Gln Phe Thr Trp Tyr Ile Asn Asn Glu Gln Val
                245                 250                 255

Arg Thr Ala Arg Pro Pro Leu Arg Glu Gln Gln Phe Asn Ser Thr Ile
                260                 265                 270

Arg Val Val Ser Thr Leu Pro Ile Thr His Gln Asp Trp Leu Arg Gly
            275                 280                 285

Lys Glu Phe Lys Cys Lys Val His Asn Lys Ala Leu Pro Ala Pro Ile
        290                 295                 300

Glu Lys Thr Ile Ser Lys Ala Arg Gly Gln Pro Leu Glu Pro Lys Val
305                 310                 315                 320

Tyr Thr Met Gly Pro Pro Arg Glu Glu Leu Ser Ser Arg Ser Val Ser
                325                 330                 335

Leu Thr Cys Met Ile Asn Gly Phe Tyr Pro Ser Asp Ile Ser Val Glu
            340                 345                 350

Trp Glu Lys Asn Gly Lys Ala Glu Asp Asn Tyr Lys Thr Thr Pro Ala
        355                 360                 365

-continued

```
Val Leu Asp Ser Asp Gly Ser Tyr Phe Leu Tyr Asn Lys Leu Ser Val
        370             375             380

Pro Thr Ser Glu Trp Gln Arg Gly Asp Val Phe Thr Cys Ser Val Met
385             390             395             400

His Glu Ala Leu His Asn His Tyr Thr Gln Lys Ser Ile Ser Arg Ser
            405             410             415

Pro Gly Lys
```

US 6,303,336 B1

HERPES VIRUS ENTRY RECEPTOR PROTEIN

CROSS-REFERENCE TO RELATED APPLICATIONS

This application is a divisional of U.S. application Ser. No. 08/509,024, filed on Jul. 28, 1995.

GOVERNMENT SUPPORT

This invention was made in part using funds obtained from the U.S. Government (National Institutes of Health Grant Nos. RO1 AI36293 and F32HI09022) and the U.S. Government may have certain rights in the invention.

TECHNICAL FIELD OF THE INVENTION

The field of this invention is a herpes virus entry receptor (HVEM). More particularly, the field of the present invention is recombinant mammalian HVEM, polynucleotides encoding that HVEM, and methods of making recombinant HVEM.

BACKGROUND OF THE INVENTION

Glycosaminoglycan chains on cell surface proteoglycans serve as receptors for the binding of herpes simplex virus types 1 and 2 (HSV-1 and HSV-2) to cells. Binding is not sufficient for entry, however: other cell surface components are necessary for virus entry, which occurs by fusion of the virion envelope with a cell membrane. For example, Chinese hamster ovary (CHO) cells express glycosaminoglycan chains to which HSV-1 and HSV-2 can bind, but are resistant to the entry of some HSV strains, particularly HSV-1(KOS).

The present invention is directed to a newly discovered protein that enables herpes simplex virus (HSV) to penetrate into cells and is a previously undiscovered member of the family of receptors designated the tumor necrosis factor receptor/nerve growth factor receptor (TNFR/NGFR) family. Members of this family have characteristic repeats of amino acid sequence containing multiple cysteines and serve as receptors for a variety of specific ligands, including but not limited to cytokines. The protein is designated herpes virus entry receptor protein or HVEM.

By identifying the gene that encodes HVEM, by showing that HVEM can mediate the entry of HSV into cells and by performing experiments to define viral and cell factors that influence the ability of HVEM to mediate HSV entry, the inventors have provided the knowledge and biological material required (i) to develop antiviral drugs that can act to block HSV (and perhaps other herpesvirus) entry into cells; (ii) to identify other members of the TNFR/NGFR family (or other cell surface molecules) that can serve as receptors for HSV-1, HSV-2 or other herpesviruses; (iii) to identify the natural ligand for the receptor; and (iv) to develop therapeutic approaches for enhancing or inhibiting action of the ligand on the receptor, depending on the pathologic or beneficial consequences of this action.

BRIEF SUMMARY OF THE INVENTION

In one aspect, the present invention provides an isolated and purified polynucleotide comprising a nucleotide sequence consisting essentially of the nucleotide of SEQ ID NO:1 from about nucleotide position 294 to about nucleotide position 1142; (b) sequences that are complementary to the sequences of (a), and (c) sequences that, when expressed, encode a polypeptide encoded by a sequence of (a). A preferred polynucleotide is a DNA molecule. In another embodiment, the polynucleotide is an RNA molecule. A preferred polynucleotide is SEQ ID NO:1.

In another embodiment, a DNA molecule of the present invention is contained in an expression vector. The expression vector preferably further comprises an enhancer-promoter operatively linked to the polynucleotide. In an especially preferred embodiment, the DNA molecule has the nucleotide sequence of SEQ ID NO:1 from about nucleotide position 294 to about nucleotide position 1142.

In another aspect, the present invention provides an oligonucleotide of from about 15 to about 50 nucleotides containing a nucleotide sequence of at least 15 nucleotides that is identical or complementary to a contiguous sequence of a polynucleotide of this invention. A preferred oligonucleotide is an antisense oligonucleotide that is complementary to a portion of the polynucleotide of SEQ ID NO:1.

The present invention also provides a pharmaceutical composition comprising a polypeptide or an antisense oligonucleotide of this invention and a physiologically acceptable diluent.

In another aspect, the present invention provides an HVEM polypeptide of mammalian origin. In one embodiment, that HVEM is an isolated and purified polypeptide of about 300 amino acid residues and comprises the amino acid residue sequence of SEQ ID NO:2. More preferably, an HVEM of the present invention is a recombinant human HVEM.

In another aspect, the present invention provides a process of making HVEM comprising transforming a host cell with an expression vector that comprises a polynucleotide of the present invention, maintaining the transformed cell for a period of time sufficient for expression of the HVEM and recovering the HVEM. Preferably, the host cell is an eukaryotic host cell such as a mammalian cell or a bacterial cell. An especially preferred host cell is a mammalian ovarian cell. The present invention also provides an HVEM made by a process of this invention. A preferred such HVEM is recombinant human HVEM.

The present invention still further provides for a host cell transformed with a polynucleotide or expression vector of this invention. Preferably, the host cell is a mammalian cell such as an ovarian cell.

BRIEF DESCRIPTION OF THE DRAWINGS

In the drawings, which form a portion of the specification:

FIGS. 2A–2B shows the nucleotide sequence of HVEM cDNA (SEQ ID NO:1) and amino acid sequence (SEQ ID NO:2) of the open reading frame. The nucleotide sequence of the cDNA insert of pBEC580 was determined as shown. Analysis of the sequence revealed the presence of a single open reading frame, the translation of which is shown below the nucleotide sequences. Features of the 283 amino acid open reading frame include a signal peptide (dashed underline), two potential sites for the addition of N-linked carbohydrate (white underline) and a hydrophobic region predicted to be a membrane spanning domain (black underline). Also indicated by the shaded amino acid sequences are the three complete and one partial cysteine rich repeats characteristic of members of the TNF/NGF receptor family.

FIG. 4A, HeLa cells (open circles) and CHO-K1 cells (closed circles). FIG. 4B, CHO cells lines stably transfected with pBEC10, which carries the HVEM cDNA [CHO-A3 (closed triangles); CHO-A12 (open squares); CHO-B3 (open triangles); CHO-B9 (closed squares); CHO-B11 (open circles)] and a control cell line stably transfected with the vector pcDNA3 [CHO-C8 (closed circles)].

FIGS. 8A–8C shows the nucleotide sequence (SEQ ID NO:6) of pBL58 and the amino acid sequence (SEQ ID NO:7) of the open reading frame encoding HVEM-Fc. Features of the HVEM ectodomain that were described in FIGS. 2A–2B are shown here along with the site at which the HVEM sequence is fused to the rabbit IgG heavy chain sequence (the boxed residues are three amino acids inserted at the fusion site due to the EcoRI linker added). The two potential sites for the addition of N-linked glycans in HVEM are underlined along with a third site in the IgG sequence.

FIG. 10 shows the relative susceptabilities of A12 cells transfected with various gD-expressing plasmids.

DETAILED DESCRIPTION OF THE INVENTION

I. The Invention

Figure 1:
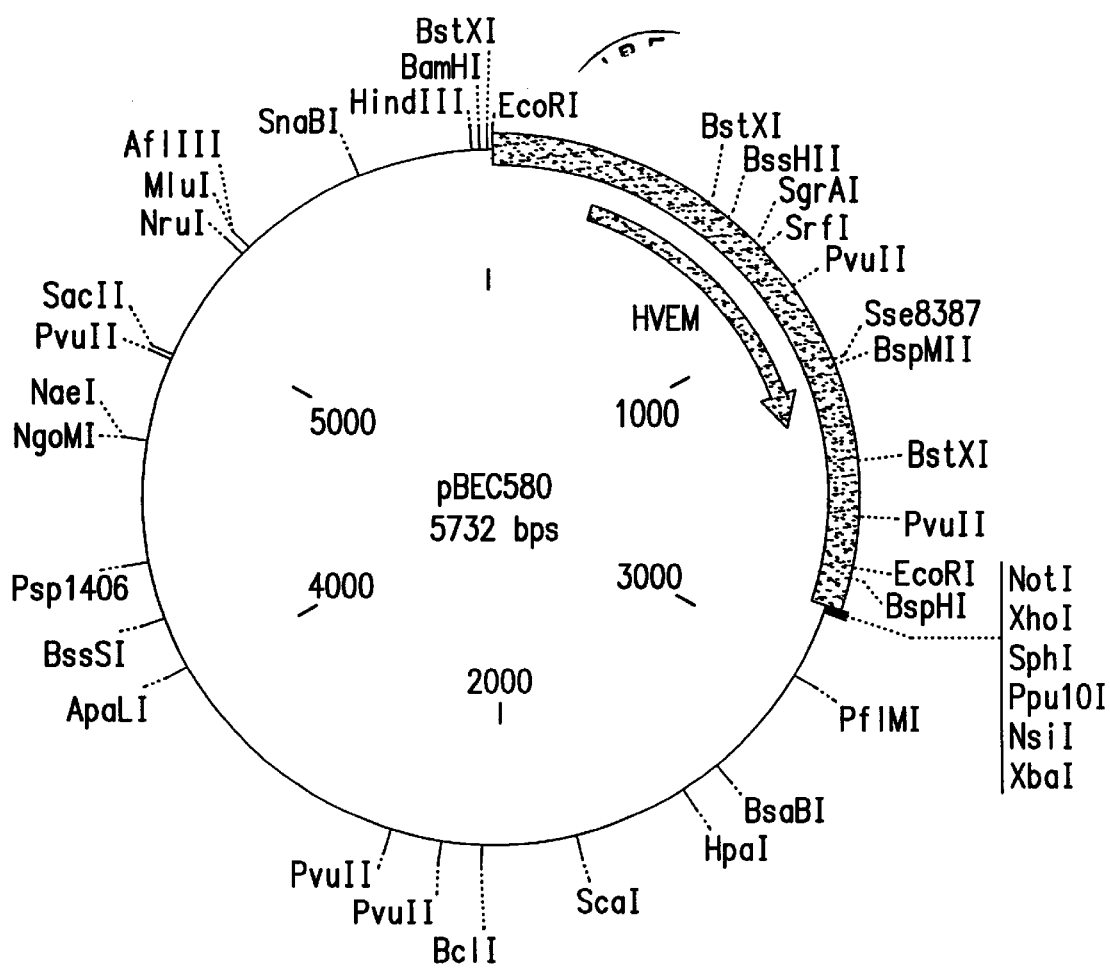
FIG. 1 shows a map of the plasmid (pBEC580) cloned from the cDNA library on the basis of its ability to convert resistant CHO-K1 cells to susceptibility to HSV-1(KOS) infection. The cDNA insert prepared as described in the text was ligated between BstXI and Not I sites in the polylinker region of pcDNAI (shown in the inset).

The present invention provides isolated and purified polynucleotides that encode HVEM of mammalian origin, expression vectors containing those polynucleotides, host cells transformed with those expression vectors, a process of making HVEM using those polynucleotides and vectors, and isolated and purified HVEM.

II. HVEM Polynucleotides

In one aspect, the present invention provides an isolated and purified polynucleotide that encodes an HVEM polypeptide of mammalian origin.

A polynucleotide of the present invention that encodes HVEM is an isolated and purified polynucleotide that comprises a nucleotide sequence consisting essentially of the nucleotide sequence of SEQ ID NO:1 from about nucleotide position 294 to about nucleotide position 1142 of SEQ ID NO:1, (b) sequences that are complementary to the sequences of (a), and (c) sequences that, when expressed, encode a polypeptide encoded by the sequences of (a). A preferred polynucleotide is a DNA molecule. In another embodiment, the polynucleotide is an RNA molecule.

A nucleotide sequence and deduced amino acid residue sequence of human HVEM are set forth in FIGS. 2A–2B. The nucleotide sequence of SEQ ID NO:1 in FIGS. 2A–2B is a full length DNA clone of human HVEM. SEQ ID NO:2 in FIGS. 2A–2B is the deduced amino acid residue sequence of that clone.

The present invention also contemplates DNA sequences which hybridize under stringent hybridization conditions to the DNA sequences set forth above. Stringent hybridization conditions are well known in the art and define a degree of sequence identity greater than about 70%–80%. The present invention also contemplates naturally occurring allelic variations and mutations of the DNA sequences set forth above so long as those variations and mutations code, on expression, for an HVER of this invention as set forth hereinafter.

As set forth above, SEQ ID NO:1, is a full length cDNA clone of human HVEM. As is well known in the art, because of the degeneracy of the genetic code, there are numerous other DNA and RNA molecules that can code for the same polypeptide as those encoded by SEQ ID NO:1. The present invention, therefore, contemplates those other DNA and RNA molecules which, on expression, encode for the polypeptide encoded by SEQ ID NO:1. Having identified the amino acid residue sequence of HVEM, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid are within the scope of this invention.

A Table of codons representing particular amino acids is set forth below in Table 1.

TABLE 1

| First position | Second Position | | | | Third position |
|---|---|---|---|---|---|
| (5' end) | T/U | C | A | G | (3' end) |
| T/U | Phe | Ser | Tyr | Cys | T/U |
|  | Phe | Ser | Tyr | Cys | C |
|  | Leu | Ser | Stop | Stop | A |
|  | Leu | Ser | Stop | Trp | G |
| C | Leu | Pro | His | Arg | T/U |
|  | Leu | Pro | His | Arg | C |
|  | Leu | Pro | Gln | Arg | A |
|  | Leu | Pro | Gln | Arg | G |
| A | Ile | Thr | Asn | Ser | T/U |
|  | Ile | Thr | Asn | Ser | C |
|  | Ile | Thr | Lys | Arg | A |
|  | Met | Thr | Lys | Arg | G |
| G | Val | Ala | Asp | Gly | T/U |
|  | Val | Ala | Asp | Gly | C |
|  | Val | Ala | Glu | Gly | A |
|  | Val | Ala | Glu | Gly | G |

A simple change in a codon for the same amino acid residue within a polynucleotide will not change the structure of the encoded polypeptide. By way of example, it can be seen from SEQ ID NO:1 (see FIGS. 2A–2B) that a CCT codon for proline exists at nucleotide positions 300–302. It can also be seen from that same sequence, however, that proline can be encoded by a CCC codon (see e.g., nucleotide positions 324–326). Substitution of the latter CCC codon for proline with the CCT codon for proline, or vice versa, does not substantially alter the DNA sequence of SEQ ID NO:1 and results in expression of the same polypeptide. In a similar manner, substitutions of codons for other amino acid residues can be made in a like manner without departing from the true scope of the present invention.

A polynucleotide of the present invention can also be an RNA molecule. A RNA molecule contemplated by the present invention is complementary to or hybridizes under stringent conditions to any of the DNA sequences set forth above. As is well known in the art, such a RNA molecule is characterized by the base uracil in place of thymidine. Exemplary and preferred RNA molecules are mRNA molecules that encode an HVEM of this invention.

The present invention also contemplates oligonucleotides from about 15 to about 50 nucleotides in length, which oligonucleotides serve as primers and hybridization probes for the screening of DNA libraries and the identification of DNA or RNA molecules that encode HVEM. Such primers and probes are characterized in that they will hybridize to polynucleotide sequences encoding HVEM or related receptor proteins. An oligonucleotide probe or primer contains a nucleotide sequence of at least 15 nucleotides that is identical to or complementary to a contiguous sequence of an HVEM polynucleotide of the present invention. Thus, where an oligonucleotide probe is 25 nucleotides in length, at least 15 of those nucleotides are identical or complementary to a sequence of contiguous nucleotides of an HVEM polynucleotide of the present invention. Exemplary HVEM polynucleotides of the present invention are set forth above.

A preferred oligonucleotide is an antisense oligonucleotide. The present invention provides a synthetic antisense oligonucleotide of less than about 50 nucleotides, preferably less than about 35 nucleotides, more preferably less than about 25 nucleotides and most preferably less than about 20 nucleotides. An antisense oligonucleotide of the present invention is directed against a DNA or RNA molecule that encodes HVEM. Preferably, the antisense oligonucleotide is directed against the protein translational initiation site or the transcriptional start site. In accordance with this preferred embodiment, an antisense molecule is directed against a region of SEQ. ID NO:1 from about nucleotide position 254 to about nucleotide position 334. It is understood by one of ordinary skill in the art that an antisense oligonucleotide can be directed either against a DNA or RNA sequence that encodes a specific target Thus, an antisense oligonucleotide of the present invention can also be directed against polynucleotides that are complementary to those shown in SEQ. ID NO:1 as well as the equivalent RNA molecules.

Preferably, the nucleotides of an antisense oligonucleotide are linked by pseudophosphate bonds that are resistant to cleavage by exonuclease or endonuclease enzymes. Preferably the pseudophosphate bonds are phosphorothioate bonds. By replacing a phosphodiester bond with one that is resistant to the action of exo-and/or endonuclease, the stability of the nucleic acid in the presence of those enzymes is increased. As used herein, pseudophosphate bonds include, but are not limited to, methylphosphonate, phosphomorpholidate, phosphorothioate, phosphorodithioate and phosphoroselenoate bonds.

An oligonucleotide primer or probe, as well as an antisense oligonucleotide of the present invention can be prepared using standard procedures well known in the art A preferred method of polynucleotide synthesis is via cyanoethyl phosphoramidite chemistry. A detailed description of the preparation, isolation and purification of polynucleotides encoding human HVEM is set forth below.

Briefly, CHO-K1 cells are resistant to the entry of HSV-1(KOS). The present invention discloses an assay to screen for human cDNAs encoding proteins capable of conferring susceptibility to HSV-1(KOS) infection on the CHO-K1 cells. Control and transfected CHO-K1 cells were exposed to a strain of HSV-1(KOS) that had been modified to express *E. coli* beta-galactosidase, under control of a human cytomegalovirus promoter, immediately after viral entry into a cell. Any transfected cells that became susceptible to HSV-1 (KOS) entry expressed beta-galactosidase after infection. Addition of the appropriate beta-galactosidase substrate (X-gal) caused the infected cells to turn blue. The high level of resistance of the CHO-K1 cells to HSV-1(KOS) infection made it possible to detect very small numbers of cells rendered susceptible to infection by transfection of the human cDNAs.

A commercially obtained unidirectional cDNA library prepared from human HeLa cell mRNA was used for the transfections. The plasmids in this library express human proteins under control of the human cytomegalovirus promoter, after transfection into eukaryotic cells. The cDNA library was purchased from Invitrogen Corp (3985 B Sorrento Valley Blvd., San Diego, Calif. 92121):

| | |
|---|---|
| catalog no. | A950-10 |
| mRNA source | HeLa cells (a human cell line derived from a carcinoma) |
| primer | oligo dT(Not I) |
| vector | pcDNAI |

This library was constructed using materials produced by Invitrogen according to the following protocol:

mRNA was isolated from the HeLa cells using the Invitrogen FastTrack® mRNA Isolation Kit. The mRNA was copied by AMV reverse transcriptase, using an oligo dT(NotI) primer, to produce the first strand of DNA. The sequence of this primer is 5'-d PO$_4$ [AACCCGGCTCGAGCGGCCGCT$_{18}$]-3' (SEQ ID NO:3). The underlined sequence is the NotI site used in a later step for cleavage of the cDNA and its insertion into the vector in a directional fashion.

The product was converted to double-stranded DNA by DNA polymerase in combination with RNaseH, and E. coli DNA ligase. Any sticky (single-stranded) ends were made blunt (filled in) by use of T4 polymerase. A BxtXI/EcoRI adapter was added to the ends by blunt-end ligation. The sequence of the adapter is: GAATTCCACCACACTTAAG-GTG (SEQ ID NO.:4). The cDNA was cut with BstXI and NotI and cloned directionally by sticky-end ligation into pcDNAI, which had also been cut with BstXI and Not I.

The plasmids were used to transform E. coli strain MC1061/P3. The number of primary recombinant plasmids was estimated to be about 1.5×10$^6$. The number of colonies in the amplified library was 4.5×10$^7$ per ml. The estimated size range of the inserts was 0.9 kb to 1.6 kb.

1.5×10$^7$ bacteria were plated (1.5×10$^5$ bacteria per large Petri plate for a total of 100 plates) to allow the growth of bacterial colonies. The colonies were scraped from each plate to yield one pool of bacteria from each plate. Samples of the 100 bacterial pools were mixed to yield 10 mixtures of 10 pools each. Plasmid DNA was extracted from each mixture of pools by standard means.

Each plasmid DNA mixture was prepared with LipofectAMINE™ (GibcoBRL), according to the manufacturer's directions, for transfection into Chinese hamster ovary cells, strain K1 (CHO-K1).

To determine whether any of the transfected cells became susceptible to HSV-1(KOS) infection, the transfected cells and control cells (untransfected or transfected with irrelevant DNA) were exposed to a mutant form of HSV-1(KOS) at an input dose sufficiently high to infect all susceptible cells. This mutant is deleted for one of the essential glycoproteins, gL, and must be propagated on gL-expressing Vero cells. The virus produced on the gL-expressing cells is fully infectious but can undergo only one round of replication because defective virus is produced in non-complementing cells. The gL open reading frame was replaced by the E. coli lacZ gene, downstream of the strong cytomegalovirus promoter. The lacZ gene encodes beta-galactosidan.

After exposure to virus for several hours, the transfected CHO-K1 cells were fixed and incubated with the beta-galactosidase substrate, X-gal. Susceptible cells were readily identified by their blue color resulting from conversion of the substrate to an insoluble blue preceipitate by the beta-galactosidase expressed after entry of the mutant HSV-1(KOS).

DNA from one mixture of ten pools was found to be positive for ability to convert some of the transfected CHO-K1 cells to susceptibility. Each of the ten bacterial pools in this mixture was tested separately by extracting plasmid DNA and repeating steps set forth above. Pool 82 was found to be positive.

Bacterial pool 82 was itself divided into 100 subpools as described above. It was found that subpool 53 was positive. The bacteria in subpool 53 were plated and 900 individual clones were picked and grown up. Plasmids DNAs were extracted from each of the clones for testing. Clone 580 was found to be positive. Clone 580 was designated pBEC580. A map of this plasmid is shown in FIG. 1.

The nucleotide sequence of the cDNA insert of pBEC580 was determined by use of the Sequenase® kit (US Biochemical Corp) according to the manufacturer's instructions.

The PCgene suite of software from Intelligenetics, Inc. was used to analyze the nucleotide sequence. As shown in FIGS. 2A–2B, one open reading frame was found in the correct orientation. The protein encoded in this open reading frame was designated a herpesvirus entry receptor protein (HVEM) and was found by sequence analysis to have properties of a type I membrane glycoprotein. Shown in FIGS. 2A–2B are 1) the predicted signal peptide that could direct translocation of the nascent peptide across membranes of the rough endoplasmic reticulum; 2) two sites that are signals for the addition of N-linked carbohydrate; and 3) a hydrophobic region that is predicted to be a membrane-spanning region, adjacent to a very basic region which could serve to anchor the protein in the membrane.

The blastp and blastn programs were used to search databases maintained by the National Center for Biotechnology Information (NCBI), National Library of Medicine, National Institutes of Health, in Bethesda, Md., for proteins or nucleotide sequences that might be identical to, or related to, those of the cDNA insert. The blastp program was used to search for HVEM-related protein sequences in the database updated daily that contains non-redundant protein sequences from five component databases (Brookhaven Protein Data Bank, the SWISS-PROT database, The PIR database, the coding sequence translations from the Gen-Bank databases and two other databases that contain cumulative weekly or daily updates, respectively, of the SWISS-PROT database and the translations from Gen Bank).

This search failed to detect any closely related proteins, indicating that HVEM has not been previously described. The blastp program identified about 30 proteins that share a characteristic sequence motif with HVEM, namely three or more cysteine-rich repeats with a characteristic pattern of 6 cysteine residues. These other proteins that are related to HVEM by this motif are all members of the TNF/NGF receptor family. They encode membrane receptors that can be triggered by the binding of specific ligands to activate specific pathways important to cell survival, apoptosis or induced protective responses against infectious agents or trauma.

The blastn program identified two entries in the DNA database (the combined non-redundant database consisting of nucleotide sequence entries from the Brookhaven Protein Data Bank, GenBank, the EMBL Data Library and cumulative daily updates of the GenBank and EMBL databases) that provide partial nucleotide sequence information for cDNAs that are very closely related to the cDNA encoding HVEM. One entry (locus HSC0BG042) provides partial sequence that is closely related to sequence in the 3' non-coding region of the HEVM cDNA. The other entry (locus HSC0BG041) provides partial sequence that is closely related to sequence in the 5' non-coding region and extending 43 amino acids into the N-terminal region of the HVEM open reading frame, but not extending into the TNF/NGF receptor motifs.

Figure 3:
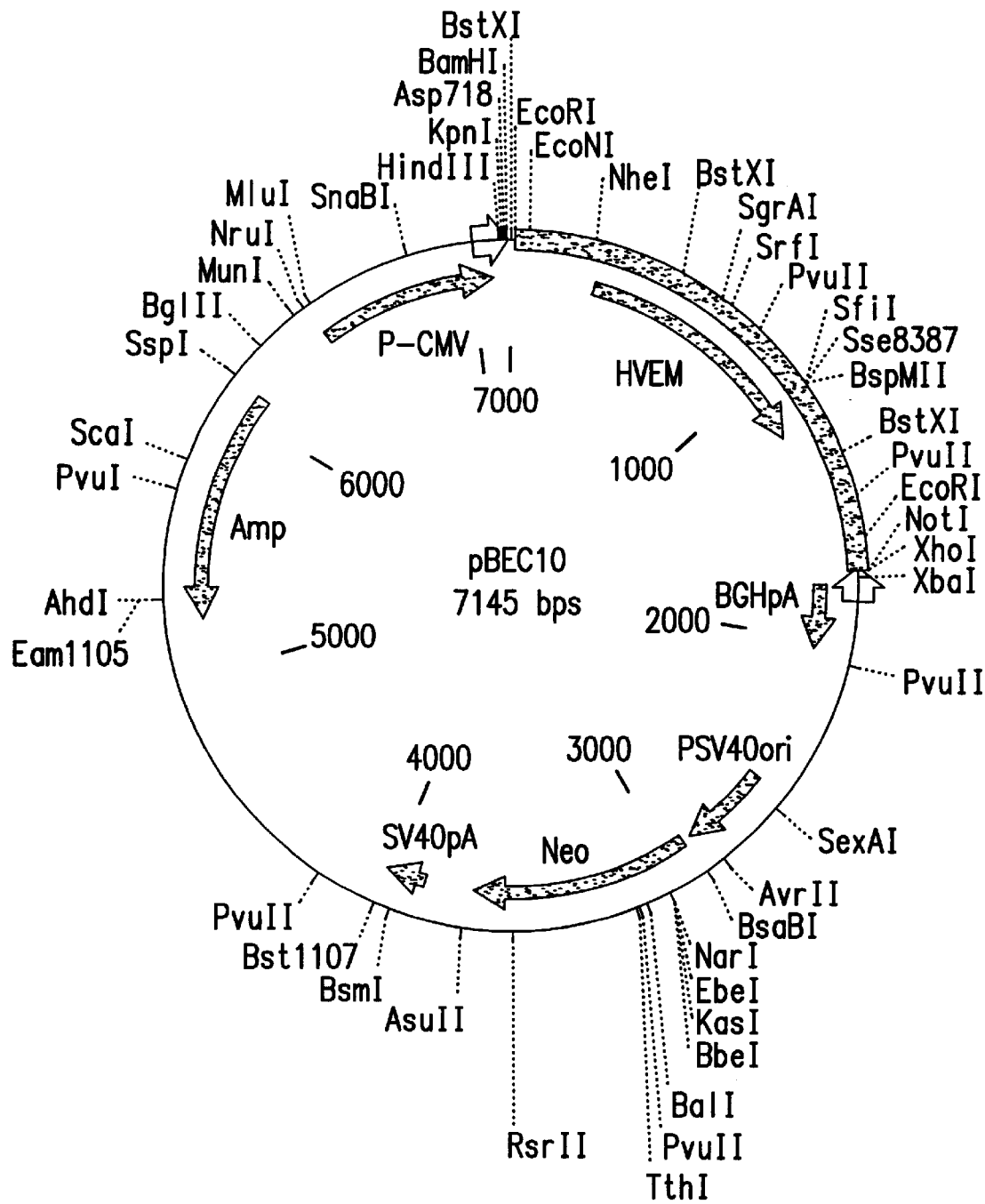
FIG. 3 shows a map of the plasmid (pBEC10) produced by transferring the cDNA insert of pBEC580 to the vector, pcDNA3 (shown in the inset). The cDNA insert was excised from pBEC580 by cutting with HindIII and XhoI and was ligated to pcDNA3 that had also been cut with HindIII and XhoI. The position of the cytomegalovirus promoter (P-CMV) is shown and also the position of the selectable marker Neo, along with upstream and downstream sequences required for its expression in eukaryotic cells.

The cDNA insert was transferred to another vector, pcDNA3, which carries a selectable marker (the neomycin gene) that can be used to isolate cell lines stably carrying the plasmid. Cells that carry and express this gene are resistant to the toxic effects of a drug called G418. The cDNA insert of pBEC580 was excised by cutting with HindIII and XhoI and the insert was ligated to pcDNA3, which had also been cut with HindIII and XhoI, to produce the new plasmid called pBEC10. A map of pBEC10 is shown in FIG. 3.

CHO-K1 cells were transfected with pBEC10 or pcDNA3 and, after about 48 hours, incubated with medium containing G418. Only cells carrying the plasmid (with the Neo marker) were able to survive.

Figure 4A:
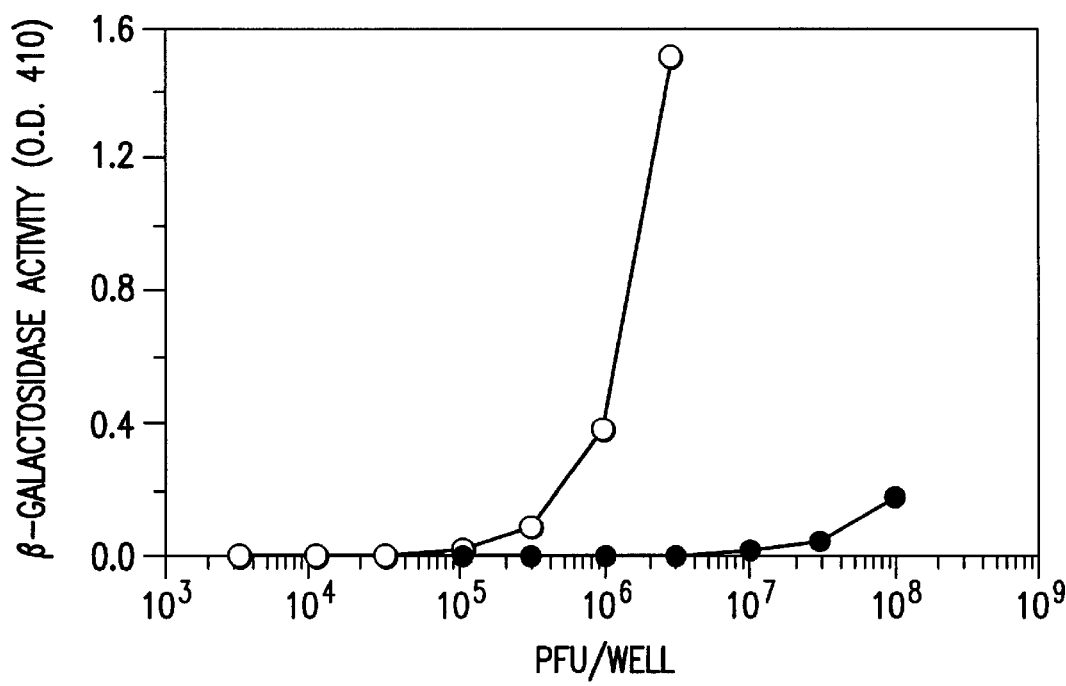
FIGS. 4A–4B shows susceptibility of HeLa cells and various CHO cell lines to infection by HSV-1(KOS). The values reported are the optical density at 410 nm. Each point represents the mean of triplicate (FIG. 4A) or quadruplicate (FIG. 4B) determinations. The individual values were within 10% of the mean.
Figure 4B:
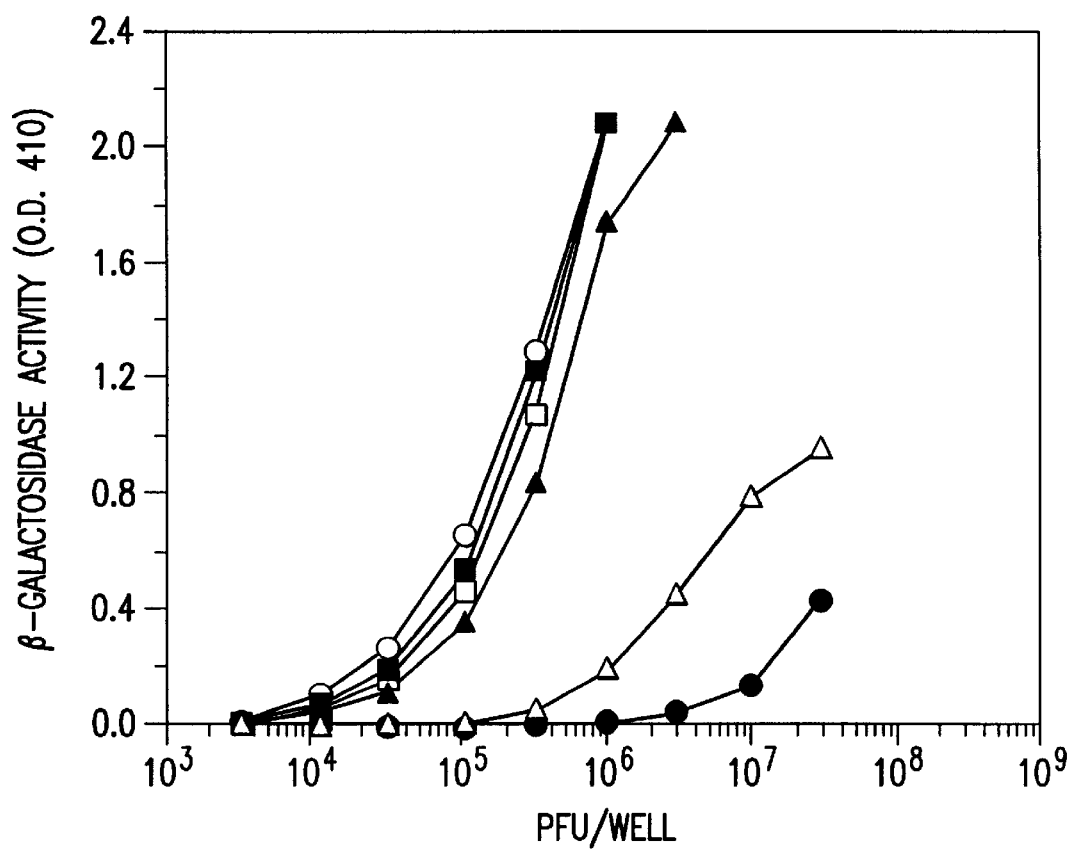
Figure 5:
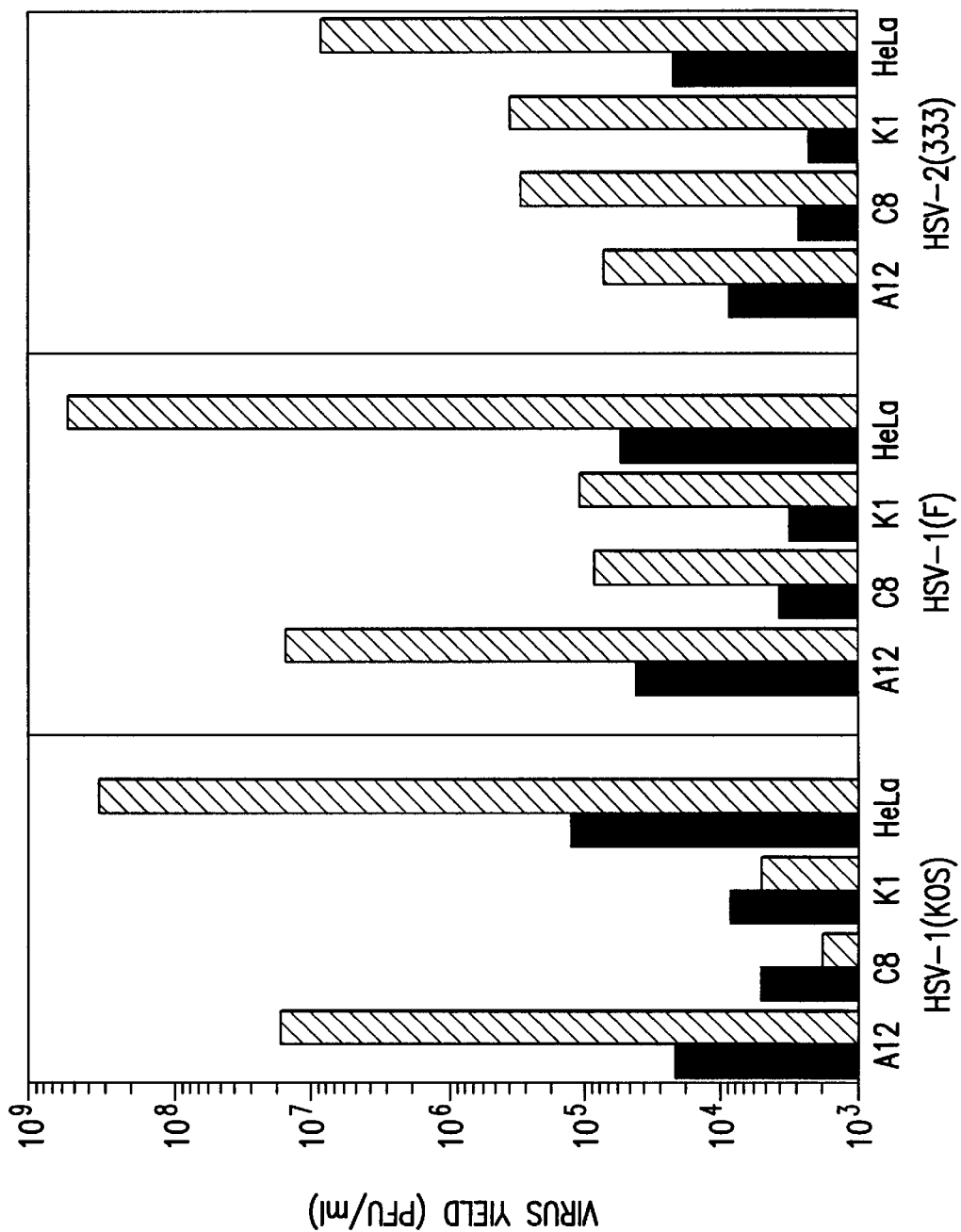
FIG. 5 shows replication of three HSV strains in CHO cells stably transfected with HVEM and in control CHO cells and HeLa cells. Cells plated in 6-well plates at about $5\times10^6$ cells per well were inoculated with the virus indicated at $10^8$ PFU per well, to ensure that all susceptible cells were synchronously infected. After allowing 2 hr for virus binding, the cells were washed and treated with citrate buffer, pH 3, to inactivate input virus that bound to cells but failed to initiate infection. Culture medium was added and one set of cultures harvested immediately (2 hr after addition of the virus inoculum) for quantitation of infectious virus by plaque assay on Vero cells, to determine the baseline viral titer prior to the appearance of progeny virus (black bars). The remainder of the cultures were harvested at 31 hr for quantitation of viral progeny (diagonal-hatched bars). The values presented represent half the yield from each culture.

Several stably transformed colonies of cells were isolated after transfection with each plasmid and were cloned. None of the clones obtained with pcDNA3 were susceptible to HSV-1(KOS) infection. About half of the clones obtained with pBEC10 were susceptible (the resistant clones may not have been able to express the protein encoded in the cDNA insert). Cells plated in 96-well dishes, at densities ranging from $10^4$ to $5 \times 10^4$ cells per well, were exposed to HSV-1 (KOS)gL86 in the quantities indicated. At 6 hr after the addition of virus, the cells were solubilized with detergent and beta-galactosidase substrate added to assess the efficiency of viral entry. Expression of beta-galactosidase signals that the virus has entered a cell and the amount of enzyme produced is proportional to the number of infected cells, at least until plateau values of beta-galactosidase activity are achieved. FIGS. 4A–4B and 5 show that CHO-K1 parental cells and CHO cells transfected with the control plasmid, pcDNA3, are resistant to HSV-1(KOS) infection whereas the cells transfected with, and stably carrying pBEC10, are susceptible to HSV-1(KOS) infection.

Although the cells transfected with the HVEM cDNA are fully susceptible to infection by HSV-1(KOS), they are resistant to infection by a mutant of HSV-1(KOS), designated HSV-1(KOS)rid1, that differs from parental virus only by an amino acid substitution in the viral envelope glycoprotein gD. This indicates that gD, at least in part, determines the ability of virus to use HVEM for entry. Because HSV-1(KOS) expressing the mutant form of gD can infect human cells almost as efficiently as parental HSV-1(KOS), there must be cell surface molecules expressed in human cells, in addition to HVEM, that can be used for entry.

CHO-A12 cells in 6-well plates were transfected with plasmids that express HSV-1 gD (pRE4) or HSV-2 gD (pWW65) under control of the Rous sarcoma virus promoter or with a control plasmid consisting of the vector with no insert (pdH). These plasmids were obtained from G. Cohen and R. Eisenberg (Univ. of Pennsylvania). Transfection was done with the LipofectAMINE™ reagent (GibcoBRL) using plasmid quantities ranging from 0.5 to 2.5 µg per well. At 24 hr after transfection, the cells were replated in 96-well plates and, 12 hr later, were exposed to HSV-1(KOS)gL86 to assess the susceptibility of the cells to infection.

Figure 6A:
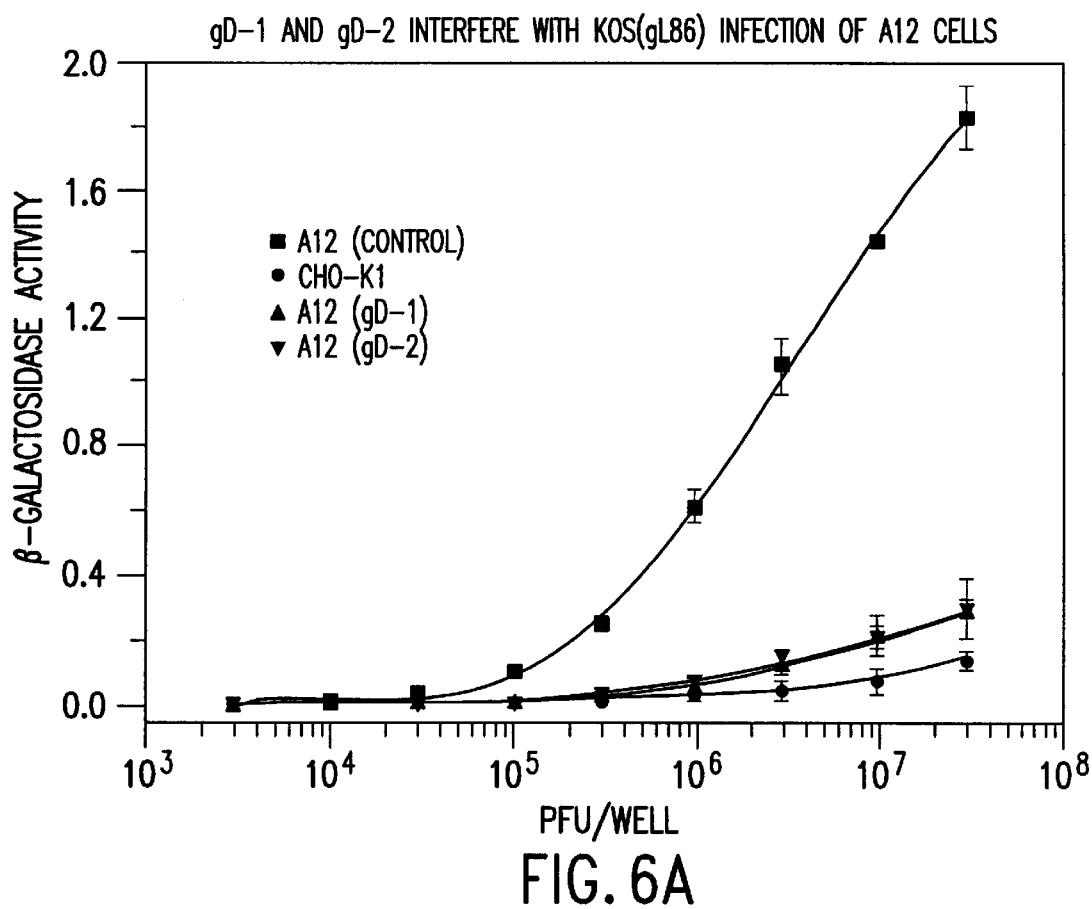
FIGS. 6A–6B shows CHO-A12 cells that express HSV-1 or HSV-2 gD are resistant to HSV-1(KOS) infection. The results shown are for the amount of plasmid DNA giving maximal interference (1.5 μg per well for the gD-1-expressing plasmid and 2.0 μg per well for the gD-2-expressing plasmid). The control plasmid was used at 1.5 μg per well and the CHO-K1 cells were not transfected. The values given are the means of quadruplicate determinations.
Figure 6B:
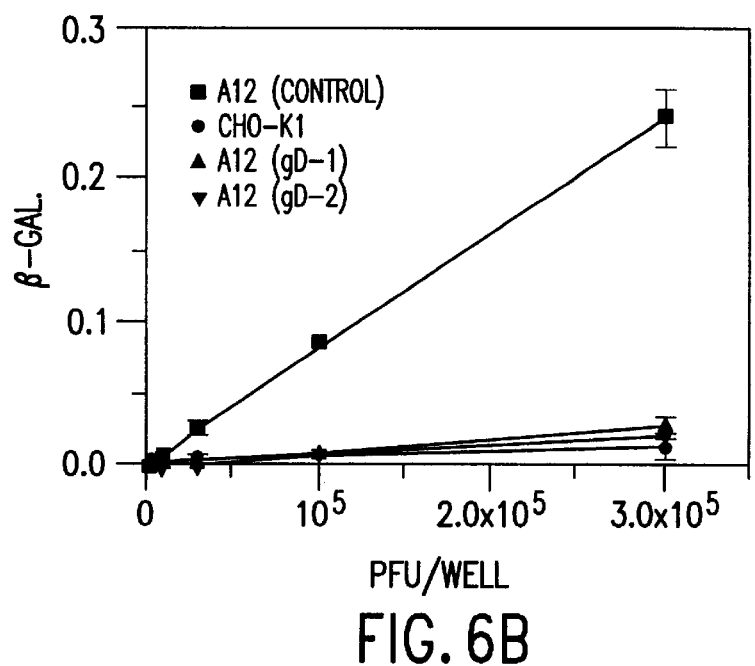

Transfection of HVEM-expressing CHO cells with a plasmid that expresses wild-type gD (either the HSV-1 or HSV-2 forms of gD) confers resistance to infection by HSV-1(KOS) (See FIGS. 6A–6B). That is an interference activity of gD that has been previously described. When gD is expressed by the cell, it can render a susceptible cell resistant to HSV-1 infection, possibly by sequestering a cell surface receptor needed for HSV-1 entry. The fact that gD expression renders the HVEM-expressing cells resistant to HSV-1(KOS) infection suggests that there may be a direct physical interaction between gD (both the HSV-1 and HSV-2 forms) and HVEM.

TABLE 2

| Cell line | Plasmid used for trans-fection | Susceptible to infection by: | | | |
|---|---|---|---|---|---|
| | | HSV-1(KOS) | HSV-1(KOS)rid1 | HSV-1(F) | HSV-2(233) |
| Cell lines obtained from others or from culture collections: | | | | | |
| HeLa (human) | None | Yes | Yes | Yes | Yes |
| Hep-2 (human) | None | Yes | Yes | Yes | Yes |
| CHO-K1 (hamster) | None | No | No | Partially | Yes |

TABLE 2-continued

| Cell line | Plasmid used for trans-fection | Susceptible to infection by: | | | |
|---|---|---|---|---|---|
| | | HSV-1(KOS) | HSV-1(KOS)rid1 | HSV-1(F) | HSV-2(233) |
| New cell lines | | | | | |
| CHO-A3 | pBEC10 | Yes | N.T.[a] | N.T.[a] | N.T.[a] |
| CHO-A12[b] | pBEC10 | Yes | NO[c] | Yes | Yes |
| CHO-B3 | pBEC10 | partially | N.T.[a] | N.T.[a] | N.T.[a] |
| CHO-B9 | pBEC10 | Yes | N.T.[a] | N.T.[a] | N.T.[a] |
| CHO-B11 | pBEC10 | Yes | N.T.[a] | N.T.[a] | N.T.[a] |
| CHO-C8 | pcDNA3 | No | No[c] | N.T.[a] | N.T.[a] |

[a]N.T.--Not tested.
[b]When the A12 cells were transfected with plasmids expressing HSV-1 or HSV-2 gD, they became resistant to HSV-1(KOS) infection.
[c]CHO-K1 cells are slightly more susceptible to infection by HSV-1(KOS) rid1 than by parental HSV-(KOS) but the expression of HVEM in the transfected cells does not enhance susceptibility of the cells to HSV-1 (KOS)rid1, in marked contrast to the results obtained with HSV-1(KOS).

Southern blot were done with digests of DNA from three human cell lines (Hep-2, HeLa and HT1080), one monkey cell line (Vero), the Chinese hamster overy cell line used for cloning HVEM (CHO-K1) and two of the CHO cell lines stably transfected with pBEC10 (CHO-A12 and CHO-B9). The probes used to detect DNA fragments with homology to HVEM were an EcoRI fragment of the HVEM cDNA insert that includes most of the insert and a smaller PvuII fragment that includes only the 3' end of the HVEM open reading frame and some of the on-coding sequence downstream. The results showed that: (i) all three human cell lines contain DNA homologous to HVEM with fragment sizes that are the same for all three cell lines in a single digest (different digests yield hybridizable bands of different sizes but the DNAs from three cell lines are indistinguishable); (ii) only a subset of the human DNA fragments that hybridize to the larger EcoRI fragment also hyubridize to the smaller PvuII fragment; (iii) the monkey cells contain weakly hybridizable DNA fragments of different sizes from those found in the human DNAs; (ic) the parental CHO-K1 cells contain no hybridizable DNA fragments; (v) the stably transfected cell lines (CHO-A12 and CHO-B9) contain DNA homologous to HVEM as predicted.

The results obtained with the human, monkey and Chinese hamster DNAs confirm that HVEM is encoded by a human cDNA and indicate that the human HVEM gene is probably a single-copy gene with multiple introns and exons, perhaps extending over a large stretch of DNA. The results also indicate that monkey cells have a gene related to human HVEM. If Chinese hamster cells have an HVEM gene, its sequence has diverged too much to be detected by a human HVEM probe.

Poly-adenylated RNAs extracted from various human tissues (heart, brain, placenta, lung, liver, skeletal muscle, kidney, and pancreas) were obtained from Clontech, Inc., as samples that had already been fractionated by electrophoresis and transferred to a membrane. The membrane was used for hybridization with the larger EcoRI probe mentioned above (almost the entire HVEM cDNA insert). The results showed that there were variable amounts of RNA homologous to HVEM in all the samples. The largest amounts were found in lung and kidney. The sizes of the bands were about 1.8 and 3.8 kb. The HVEM cDNA insert claimed in the application is about 1.8 kb.

III. HVEM Polypeptides

In another aspect, the present invention provides an HVEM polypeptide of mammalian origin. An HVEM of the present invention is a polypeptide of about 293 amino acid residues. Preferably, an HVEM is a human HVEM. A human form of HVEM is shown in SEQ ID NO:2. Thus, human HVEM can be defined as a polypeptide of about 300 or less amino acid residues comprising the amino acid residue sequence of SEQ ID NO:2.

The present invention also contemplates amino acid residue sequences that are substantially duplicative of the sequences set forth herein such that those sequences demonstrate like biological activity to disclosed sequences. Such contemplated sequences include those sequences characterized by a minimal change in amino acid residue sequence or type (e.g., conservatively substituted sequences) which insubstantial change does not alter the basic nature and biological activity of HVEM.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

Figure 7:
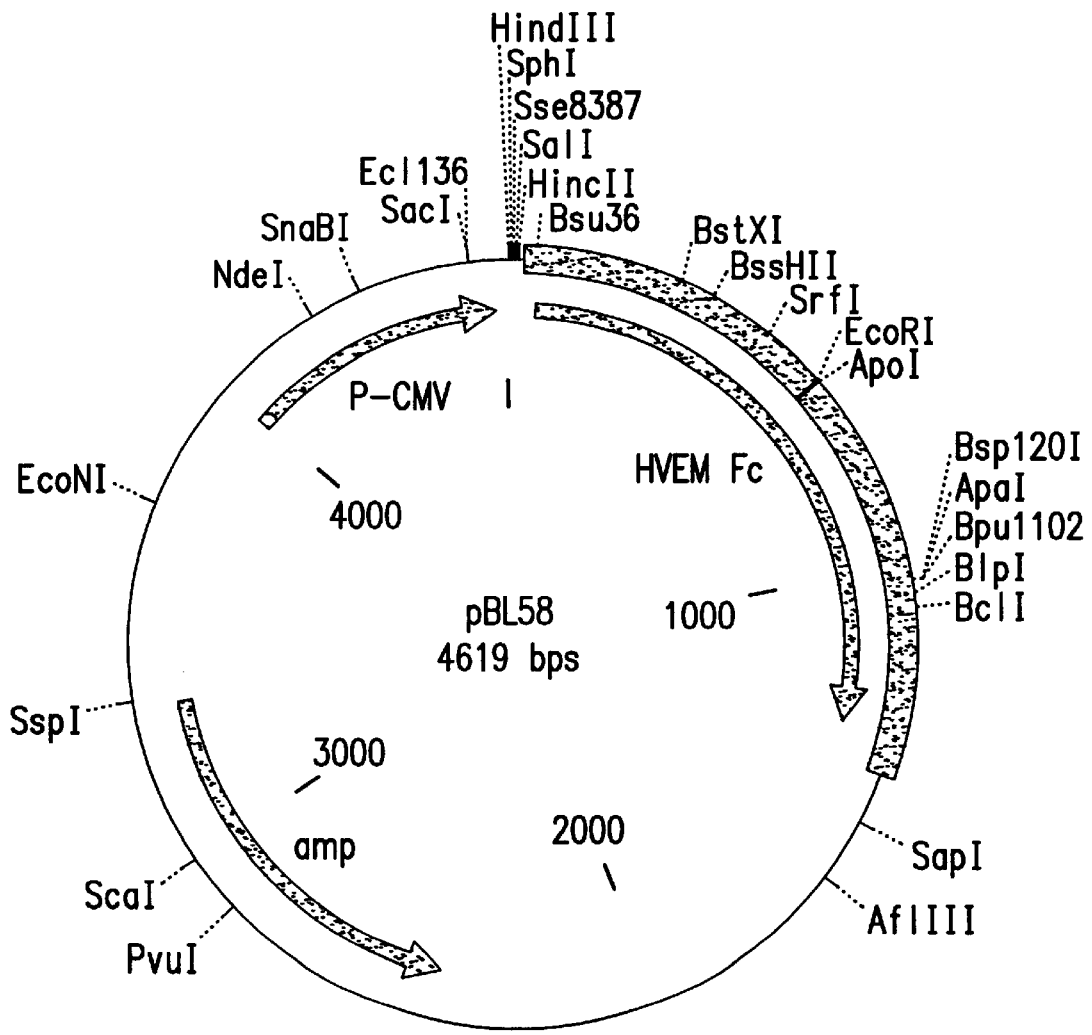
FIG. 7 shows a map of the plasmid (pBL58) expressing the HVEM-Fc hybrid protein.
Figure 9:
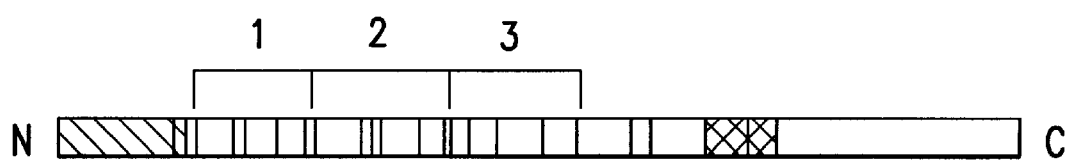
FIG. 9 shows a schematic drawing of human HVEM. The protein has characteristics of a typical type I membrane glycoprotein, including an N-terminal signal sequence (diagonal-hatched box) and a membrane-spanning region (cross-hatched box). The protein also has the cysteine-rich repeats characteristic of the TNFR/NGFR family of cell surface receptors. Each repeat has 4–6 cysteine residues (represented by vertical lines).

A comparison of the amino acid sequence SEQ ID NO:2 with the protein databases maintained at the National Library of Medicine (NIH) and with a computer program designed to detect functional motifs in proteins revealed that HVEM has not previously been described, that it is not closely related to other proteins in the database, but that it has three copies of a cysteine-rich motif found in members of the TNFR/NGFR family. heavy chain fragment This latter fragment was prepared for the ligation by using PCR technology to insert an EcoRI site just upstream of the following rabbit sequence (ACAAGACCGTTGCACCCTC) (SEQ ID NO:5). Cleavage at this EcoRI site, followed by filling-in, permitted blunt-end ligation to the PvuII site of HVEM so that the two open reading frames were joined in the same reading frame. The 3' end of the rabbit cDNA insert was cut with PstI and joined to the HindIII site of pGEM4 by blunt-end ligation (the PstI cut end was trimmed and the HindIII cut end was filled in). The vector sequences are from pGEM4 and include sequences extending to a unique NheI site that was joined by sticky-end ligation to an SpeI site adjacent to the cytomegalovirus promoter (P-CMV) from pcDNAneo. The other end of the P-CMV region was cut with HindIII and is joined to the HindIII site at the top of the map. (FIG. 7)

Expression of the hybrid protein has been demonstrated both in Vero cells and in CHO-K1 cells. The protein is secreted into the medium, as predicted, since it should have a signal sequence for translocation into the cell's secretory pathway but has no membrane-spanning region to anchor it to a membrane. The hybrid protein is readily detected on Western blots by use of commercially available antibodies specific for the constant regions of rabbit IgG.

Treatment of the hybrid protein with various glycosidases (endoH, endoF and endoO) has revealed that the protein carries N-linked glycans of the complex type, which is characteristic for secreted proteins, and also carries O-linked glycans, as predicted. This hybrid protein is used to screen for mouse monoclonal antibodies specific for HVEM and to identify HSV proteins with which it might interact.

The hybrid gene is contained in two different expression plasmids, the latter of which contains a selectable marker for obtaining transformed cells that stably carry the plasmid. Transfection of these including pGEM3, pGEM4 and pcDNAneo. Starting from the HindIII site of pBL58, part of the polylinker from pGEM3 (HindIII site to XbaI site) was linked to a sticky end created by cutting the HVEM insert with NheI about 37 nucleotides upstream of the HVEM start codon. Another cleavage of the HVEM insert at a PvuII site within the open reading frame created a blunt end that was blunt-end ligated to the rabbit IgG heavy chain fragment. This latter fragment was prepared for the ligation by using PCR technology to insert an EcoRI site just upstream of the following rabbit sequence (ACAAGACCGTTGCACCCTC) (SEQ ID NO:5). Cleavage at this EcoRI site, followed by filling-in, permitted blunt-end ligation to the PvuII1 site of HVEM so that the two open reading frames were joined in the same reading frame. The 3' end of the rabbit cDNA insert was cut with PstI and joined to the HindIII site of pGEM4 by blunt-end ligation (the PstI cut end was trimmed and the HindIII cut end was filled in). The vector sequences are from pGEM4 and include sequences extending to a unique NheI site that was joined by sticky-end ligation to an SpeI site adjacent to the cytomegalovirus promoter (P-CMV) from pcDNAneo. The other end of the P-CMV region was cut with HindIII and is joined to the HindIII site at the top of the map (See SEQ ID NO:6, FIGS. 8A–8C).

Expression of the hybrid protein (SEQ. ID. NO:7, FIGS. 8A–8C) has been demonstrated both in Vero cells and in CHO-K1 cells. The protein is secreted into the medium, as predicted, since it should have a signal sequence for translocation into the cell's secretory pathway but has no membrane-spanning region to anchor it to a membrane. The hybrid protein is readily detected on Western blots by use of commercially available antibodies specific for the constant regions of rabbit IgG.

Treatment of the hybrid protein with various glycosidases (endoH, endoF and endoO) has revealed that the protein carries N-linked glycans of the complex type, which is characteristic for secreted proteins, and also carries O-linked glycans, as predicted. This hybrid protein is used to screen for mouse monoclonal antibodies specific for HVEM and to identify HSV proteins with which it might interact.

The hybrid gene is contained in two different expression plasmids, the latter of which contains a selectable marker for obtaining transformed cells that stably carry the plasmid.

Transfection of these plasmids into cells has revealed expression of a hybrid polypeptide of molecular weight approximately 60,000 after dissociation into its component chains.

This hybrid polypeptide, designated HVEM/Fc, carries N-linked glycans and is expressed as a dimer held together by disulfide bonds (this is characteristic of hybrid proteins prepared with IgG domains that can dimerize to form the Fc region). Commercially available antibodies specific for rabbit IgG were used to detect HVEM/Fc in Western blots and in ELISA assays.

The observed apparent size of the hybrid protein is similar to the size predicted, provided the predicted molecular weight includes about 10,000 for the added carbohydrate.

Evidence has been obtained that HVEM is only one of several cell surface receptors that can mediate the entry of HSV-1 and HSV-2 into cells and that functional use of HVEM (and perhaps other receptors) is determined by the structure of the virion envelope glycoprotein gD. A mutant of HSV-1(KOS), designated HSV-1(KOS)rid1 has a single amino acid substitution in gD that confers resistance to gD-mediated interference with HSV infection and alters slightly the ability of this virus, relative to the wild-type parental strain, to penetrate into various cell types including CHO cells and human cells. By use of a mutant strain of HSV-1(KOS) that is deleted for gD and complemented by replication in cells expressing either the wild-type or mutant form of gD it has been shown that HVEM expression renders CHO cells fully susceptible to infection by virus carrying wild-type gD but not to infection by virus carrying mutant gD, despite the fact that both viruses could infect human cells with nearly equal efficiency. The implications of this result are several-fold.

First, the result shows that the structure of gD determines whether HVEM can be used as a receptor for entry, raising the possibility of a direct physical interaction. This is consistent with knowledge that gD is one of at least four envelope glycoproteins required for HSV entry. Second, although HVEM is expressed in cultured human cells, such as HeLa cells (the cDNA library used was prepared from HeLa cells), there must be other receptors expressed in human cells that can facilitate the entry of HSV-1(KOS) carrying the mutant form of gD. Third, because CHO-K1 cells are so resistant to HSV-1(KOS) carrying the rid1 form of gD, it is possible to use the gD-negative mutant of HSV-1(KOS), which expresses beta-galactosidase and can be complemented with the rid1 form of gD, to screen for expression of the human gene or genes that can facilitate the entry of HSV-1(KOS)rid1 into CHO-K1 cells.

The possibility exists that several members of the TNFR/NGFR family can serve as receptors for entry of HSV-1, HSV-2 or other herpesviruses, and that the particular receptor favored by a given herpesvirus or strain is determined at least in part by the structure of gD.

Expression of HVEM in CHO-K1 cells significantly enhances the entry of at least two HSV-1 strains. Because the original CHO cells are fully susceptible to entry of the HSV-2 strains tested, it is not possible to assess directly whether HVEM has any effect on HSV-2 entry into CHO-K1 cells. Cells expressing HSV gD become resistant, however, to HSV-1 and HSV-2 infection, and also to infection with related alphaherpesviruses, because of a block to penetration (binding is unimpaired by gD expression). This phenomenon has been called gD-mediated interference.

The fact that HSV-1 gD can interfere with infection by HSV-1, HSV-2 or other herpesviruses implies that all the herpesviruses may use an overlapping set of receptors for entry. Transient expression of gD in CHO cells already expressing HVEM renders the cells resistant to HSV-1 (KOS) entry. Both the HSV-2 and HSV-1 forms of wild-type gD are able to interfere with ability of HSV-1(KOS) to use HVEM for entry, suggesting that both forms can interact with HVEM for interference and possibly also for entry. As predicted from the hypothesis about the mechanism of interference, the rid1 form of gD is impaired in ability to mediate interference in HVEM-expressing CHO cells (consistent with the finding that virus carrying the rid1 form of gD is impaired in ability to enter HVEM-expressing CHO cells).

The interference activity of gD can be quantitated by transfecting gD-expressing plasmids into HVEM-expressing CHO cells and then exposing the cells to HSV-1(KOS)gL86 to determine whether the cells are susceptible or resistant to viral entry. This provides an assay for testing the interference activity of various fD mutants, in order to define the structural features of fD that are required for interference. A number of mutant forms of gD produced by others (G. Cohen and R. Eisenberg of the Univ. of Pennsylvania) have already been tested by others to determine whether the mutations alter gD function in the virion (function required for viral entry into cells). These same mutant forms of gD (provided by G. Cohen and R. Eisenberg) are being tested for their interference actibity. Results obtained to date are summarized in FIG. 10. CHO-A12 cells, which stably express HVEM, were plated on 6-well dishes and transfected with one of several plasmids that express different forms of gD. At 24 hr after transfection, the cells were replated in 96-well plates and 12 hr later they were exposed to HSV-1(KOS)gL86 at several concentrations. At 6 hr after adding virus, the cells were solubilized and β-galactosidase substrate was added. The colored product was quantitated by spectromophotometry. Selecting the values obtained (OD410) at a dose of virus where the amount of virus added was directly proportional to the amount of β-galactosidase detected, the data were normalized for comparison by dividing the bvalues obtained for cells transfected with a gD-expressing plasmid by the value obtained for cells transfected with a control plasmid (control). The forms of gD expressed by the various plasmids were wild-type gD-1 (pRE4), which is 369 amino acids in length, wild-type gD-2 (pWW65), mutant gD-1 deleted for amino acids 196–207 (pWW13), mutant gD-1 deleted for amino acids 234–244 (pWW17), mutant gD-1 deleted for amino acids 194–287 (pWW49), mutant gD-1 deleted for amino acids 234–287 (pWW52), mutant gD-1 deleted for amino acids 208–287 (pWW61), mutant gD-1 with a substitution that replaces Glu with Asp at position 63 (pWW62), mutant gD-1 deleted for amino acids 338–369 (pWW63) and mutant gD-1 with a substitution that replaces Gln with Pro at position 27 (pMW13). Low (-galactosidase activity implies that the transfected gD had interference activity; high activity indicates that the transfected gD had reduced or no activity. All plasmids used except pMW13 were obtained from G. Cohen and R. Eisenberg (Univ. of Pennsylvania). The results indicate that deletions or alterations of gD between the middle and membrane-spanning region of the molecule eliminate interference activity whereas deletion of the cytoplasmic tail of gD and an amino acid substitution at position 63 are without effect. An amino acid substitution at position 27 (the rid1 mutation) reduces, but does not eliminate, interference activity. From the results obtained to date, it appears that alterations affecting the function of gD in infectivity also affect its function in interference. This is consistent with the hypothesis that gD interference results from competition between cell-associated gD and virion-associated gD for a common target, possibly HVEM.

An HVEM polypeptide of the present invention has numerous uses. By way of example, such a polypeptide can be used in a screening assay for the identification of drugs or compounds that inhibit or augment the action of HVEM (e.g., agonist and antagonist to HSV entry into a cell). A screening assay for the identification of such compound, therefore, can be established whereby the ability of a compound to alter the action of HVEM can be determined by exposing cells to HSV in the presence of a polypeptide of the present invention and varying amounts of compounds suspected of inhibiting the activity of HVEM.

The hybrid protein HVEM/Fc is being used to immunize rabbits for the production of polyclonal antisera specific for the HVEM portion of the molecule. In addition the hybrid protein is used to screen for hybridomas secreting antibodies specific for the HVEM portion (the mice were immunized with HVEM-expressing CHO cells). The hybrid protein is used to determine whether a physical interaction between the hybrid protein and gD or other viral proteins can be detected. The hybrid protein also has use in screening expression cDNA libraries for natural ligands of HVEM and screening compounds for inhibitors of the interaction between HSV virions and HVEM.

In addition, an HVEM polypeptide of the present invention can be used to produce antibodies that immunoreact specifically with HVEM. Means for producing antibodies are well known in the art. An antibody directed against HVEM can be a polyclonal or a monoclonal antibody.

Antibodies against HVEM can be prepared by immunizing an animal with an HVEM polypeptide of the present invention. Means for immunizing animals for the production of antibodies are well known in the art. By way of an example, a mammal can be injected with an inoculum that includes a polypeptide as described herein above. The polypeptide can be included in an inoculum alone or conjugated to a carrier protein such as keyhole limpet hemocyanin (KLH). The polypeptide can be suspended, as is well known in the art, in an adjuvant to enhance the immunogenicity of the polypeptide. Sera containing immunologically active antibodies are then produced from the blood of such immunized animals using standard procedures well known in the art.

The identification of antibodies that immunoreact specifically with HVEM is made by exposing sera suspected of containing such antibodies to a polypeptide of the present invention to form a conjugate between antibodies and the polypeptide. The existence of the conjugate is then determined using standard procedures well known in the art.

An HVEM polypeptide of the present invention can also be used to prepare monoclonal anti'bodies against HVEM and used as a screening assay to identify such monoclonal antibodies. Monoclonal antibodies are produced from hybridomas prepared in accordance with standard techniques such as that described by Kohler et al. (Nature, 256:495, 1975). Briefly, a suitable mammal (e.g., BALB/c mouse) is immunized by injection with a polypeptide of the present invention. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against HVEM. Screening of the cell culture medium is made with a polypeptide of the present invention.

IV. Method of Making HVEM

In another aspect, the present invention provides a process of making HVEM. In accordance with that process, a suitable host cell is transformed with a polynucleotide of the present invention. The transformed cell is maintained for a period of time sufficient for expression of the HVEM. The formed HVEM is then recovered.

Means for transforming host cells in a manner such that those cells produce recombinant polypeptide are well known in the art. Briefly, a polynucleotide that encodes the desired polypeptide is placed into an expression vector suitable for a given host cell. That vector can be a viral vector, phage or plasmid. In a preferred embodiment, a host cell used to produce HVEM is an eukaryotic host cell and an expression vector is an eukaryotic expression vector (i.e., a vector capable of directing expression in a eukaryotic cell). Such eukaryotic expression vectors are well known in the art.

In-another embodiment, the host cell is a bacterial cell. An especially preferred bacterial cell is an *E. coli*. Thus, a preferred expression vector is a vector capable of directing expression in *E. coli*.

A polynucleotide of an expression vector of the present invention is preferably operatively associated or linked with an enhancer-promoter. A promoter is a region of a DNA molecule typically within about 100 nucleotide pairs in front of (upstream of) the point at which transcription begins. That region typically contains several types of DNA sequence elements that are located in similar relative positions in different genes. As used herein, the term "promoter" includes what is referred to in the art as an upstream promoter region or a promoter of a generalized RNA polymerase transcription unit.

Another type of transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from a transcription start site so long as the promoter is present.

As used herein, the phrase "enhancer-promoter" means a composite unit that contains both enhancer and promoter elements. An enhancer promoter is operatively linked to a coding sequence that encodes at least one gene product. As used herein, the phrase "operatively linked" or its grammatical equivalent means that a regulatory sequence element (e.g. an enhancer-promoter or transcription terminating region) is connected to a coding sequence in such a way that the transcription of that coding sequence is controlled and regulated by that enhancer-promoter. Means for operatively linking an enhancer-promoter to a coding sequence are well known in the art An enhancer-promoter used in an expression vector of the present invention can be any enhancer-promoter that drives expression in a host cell. By employing an enhancer-promoter with well known properties, the level of expression can be optimized. For example, selection of an enhancer-promoter that is active in specifically transformed cells permits tissue or cell specific expression of the desired product. Still further, selection of an enhancer-promoter that is regulated in response to a specific physiological signal can permit inducible expression.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Enhancer-promoters and transcription-terminating regions are well known in the art. The selection of a particular enhancer-promoter or transcription-terminating region will depend, as is also well known in the art, on the cell to be transformed.

A clone of the human form of HVEM was identified by DNA sequence analysis as set forth above. This clone was used in all subsequent expression studies. HVEM was expressed in CHO-K1 cells under the control of a human cytomegalovirus promoter.

Expression vectors containing the encoding DNA sequence for all or a portion of human HVEM are designated pBEC580, pBEC10, and pBL58. Both vectors were deposited, under the terms of the Budapest Treaty, on Jul. 28, 1995 in the American Type Culture Collection, 12301 Parklawn Drive, Rockville, Md. 20852, and have been assigned ATCC Accession Nos: 97236(pBEC580), 97235 (pBEC10), and 97237(pBL58).

The present invention also contemplates a host cell transformed with a polynucleotide or expression vector of this invention. Means for transforming cells and polynucleotides and expression vectors used to transform host cells are set forth above. Preferably, the host cell is an eukaryotic host cell such as a mammalian cell or a prokaryotic cell such as an E. coli.

V. Pharmaceutical Compositions

The present invention also provides a pharmaceutical composition comprising a polypeptide or a polynucleotide of this invention and a physiologically acceptable diluent.

In a preferred embodiment, the present invention includes one or more antisense oligonucleotides or polypeptide, as set forth above, formulated into compositions together with one or more non-toxic physiologically tolerable or acceptable diluents, carriers, adjuvants or vehicles that are collectively referred to herein as diluents, for parenteral injection, for oral administration in solid or liquid form, for rectal or topical administration, or the like.

The compositions can be administered to humans and animals either orally, rectally, parenterally, intracisternally, intravaginally, intraperitoneally, locally, or as a buccal or nasal spray.

Compositions suitable for parenteral administration can comprise physiologically acceptable sterile aqueous or non-aqueous solutions, dispersions, suspensions or emulsions and sterile powders for reconstitution into such sterile solutions or dispersions. Examples of suitable diluents include water, ethanol, polyols, suitable mixtures thereof, vegetable oils and injectable organic esters such as ethyl oleate. Proper fluidity can be maintained, for example, by the use of a coating such as lecithin, by the maintenance of the required particle size in the case of dispersions and by the use of surfactants.

Compositions can also contain adjuvants such as preserving, wetting, emulsifying, and dispensing agents. Prevention of the action of microorganisms can be insured by various antibacterial and antifungal agents, for example, parabens, chlorobutanol, phenol sorbic acid, and the like. It may also be desirable to include isotonic agents, for example, sugars, sodium chloride and the like. Prolonged absorption of the injectable pharmaceutical form can be brought about by the use of agents delaying absorption, for example, aluminum monostearate and gelatin.

Besides such inert diluents, the composition can also include sweetening, flavoring and perfuming agents. Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonit, agar-agar and tragacanth, or mixtures of these substances, and the like.

The invention has been described in terms of preferred embodiments. One of ordinary skill in the art readily appreciates that changes and modifications can be made to those embodiments without departing from the true scope of this invention.

Deposit: Under the terms of the Budapest Treaty on the International Recognition of the Deposit of Microorganisms for the Purpose of Patent Procedure, deposit of the plasmids pBEC10, pBEC580 and pBL58 has been made on Jul. 28, 1995, with the American Type Culture Collection (ATCC) of Rockville, Md., USA, where the deposits were given ATCC Accession Numbers ATCC 97235, ATCC 97236 and ATCC 97237, respectively.

Applicant's assignee, Northwestern University, represents that the ATCC is a depository afforded permanence of the deposit and ready accessibility thereto by the public if a patent is granted. All restrictions on the availability to the public of the material so deposited will be irrevocably removed upon granting of a patent. The material will be readily available during the pendency of the patent application to one determined by the Commissioner to be entitled thereto under 37 C.F.R. § 1.14 and 35 U.S.C. § 122. The deposited material will be maintained with all the care necessary to keep it viable and uncontaminated for a period of at least five years after the most recent request for the furnishing of a sample of the deposited material, and in any case, for a period of at least thirty (30) years after the date of the deposit or for the enforceable life of the patent, whichever period is longer. Applicant's assignee acknowledges its duty to replace the deposit should the depository be unable to furnish a sample when requested due to the condition of the deposit.

What is claimed is:

1. An isolated and purified polypeptide of about 300 amino acid residues, wherein said polypeptide is encoded by a cDNA contained within the plasmid pBEC580, designated as ATCC No. 97236.

2. A recombinant human HVEM polypeptide, wherein said polypeptide is encoded by a cDNA contained within the plasmid pBEC580, designated as ATCC No. 97236.

3. The recombinant human HVEM polypeptide of claim 2, wherein said cDNA is the sequence of SEQ ID NO:1 from nucleotide position 294 to nucleotide position 1142.

4. A recombinant human HVEM made by the process of transforming a host cell with an expression vector comprising a cDNA contained within the plasmid pBEC580, designated as ATCC No. 97236, maintaining the transformed cell for a period of time sufficient for expression of said HVEM, and recovering said HVEM from said cell.

5. An isolated and purified polypeptide encoded by a cDNA contained within the plasmid pBL58 (ATCC No. 97237), wherein said polypeptide comprises a rabbit immunoglobulin heavy chain amino acid sequence.

6. An isolated and purified polypeptide encoded by a cDNA contained within the plasmid pBL58 (ATCC No. 97237), wherein said cDNA comprises a nucleotide sequence which encodes soluble HVEM and does not comprise a nucleotide sequence which encodes rabbit immunoglobulin heavy chain.

7. An isolated and purified polypeptide encoded by a cDNA contained within the plasmid pBL58 (ATCC No. 97237), wherein said polypeptide comprises amino acids 1–185 of human HVEM.

8. An isolated and purified polypeptide comprising soluble HVEM, wherein said soluble HVEM comprises an amino acid sequence encoded by a cDNA contained within the plasmid pBL58 (ATCC No. 97237), and further wherein said soluble HVEM does not comprise a rabbit immunoglobulin heavy chain amino acid sequence.

9. A cell transformed with a nucleic acid encoding a recombinant human HVEM polypeptide, wherein said polypeptide is encoded by a cDNA contained within the plasmid pBEC580, designated as ATCC NO. 97236.

10. The cell of claim 9, wherein said cell is a mammalian cell.

11. The cell of claim 10, wherein said cell is an ovarian cell.

12. The cell of claim 11, wherein said ovarian cell is selected from the group consisting of CHO-A3, CHO-A12, CHO-B3, CHO-B9 and CHO-B11.

13. The cell of claim 9, wherein said cell is a bacterial cell.

14. A method of making a recombinant human HVEM, said method comprising transforming a host cell with an expression vector comprising a cDNA contained within the plasmid pBEC580, designated as ATCC No. 97236, maintaining the transformed cell for a period of time sufficient for expression of said HVEM, and recovering said HVEM from said cell.

15. The method of claim 14, wherein said host cell is a eukaryotic cell.

16. The method of claim 15, wherein said eukaryotic cell is an ovarian cell.

17. The method of claim 16, wherein said HVEM is encoded by SEQ ID NO:1 from nucleotide position 294 to nucleotide position 1142, wherein SEQ ID NO:1 is contained with the plasmid pBEC580, designated as ATCC No. 97236.

18. A cell transformed with a nucleic acid encoding a polypeptide, said polypeptide comprising soluble HVEM, wherein said soluble HVEM comprises an amino acid sequence encoded by a cDNA contained within the plasmid pBL58 (ATCC No. 97237), and further wherein said soluble HVEM does not comprise a rabbit immunoglobulin heavy chain amino acid sequence.

19. The cell of claim 18, wherein said cell is a mammalian cell.

20. The cell of claim 19, wherein said cell is an ovarian cell.

21. The cell of claim 20, wherein said ovarian cell is selected from the group consisting of CHO-A3, CHO-A12, CHO-B3, CHO-B9 and CHO-B11.

22. The cell of claim 18, wherein said cell is a bacterial cell.

23. A method of making a soluble human HVEM, said method comprising transforming a host cell with an expression vector comprising a cDNA contained within the plasmid pBL58, designated as ATCC No. 97237, maintaining the transformed cell for a period of time sufficient for expression of said HVEM, and recovering said HVEM from said cell.

24. The method of claim 23, wherein said host cell is a eukaryotic cell.

25. The method of claim 24, wherein said eukaryotic cell is an ovarian cell.

26. The method of claim 23, wherein said soluble HVEM comprises an amino acid sequence encoded by a cDNA contained within the plasmid pBL58 (ATCC No. 97237), and further wherein said soluble HVEM does not comprise a rabbit immunoglobulin heavy chain amino acid sequence.

* * * * *

UNITED STATES PATENT AND TRADEMARK OFFICE
CERTIFICATE OF CORRECTION

PATENT NO.    : 6,303,336 B1  
DATED         : July 17, 2003  
INVENTOR(S)   : Spear et al.

It is certified that error appears in the above-identified patent and that said Letters Patent is hereby corrected as shown below:

<u>Column 1,</u>
Line 13, change "F32HI09022" to -- F32AI09022 --.

Signed and Sealed this

Second Day of September, 2003

JAMES E. ROGAN
*Director of the United States Patent and Trademark Office*